(12) United States Patent
Vorster

(10) Patent No.: US 12,343,165 B2
(45) Date of Patent: Jul. 1, 2025

(54) SELF CONTAINED MONITOR AND SYSTEM FOR USE

(71) Applicant: Vitls Inc., Houston, TX (US)

(72) Inventor: Werner Vorster, Houston, TX (US)

(73) Assignee: Vitls Inc., Houston, TX (US)

( * ) Notice: Subject to any disclaimer, the term of this patent is extended or adjusted under 35 U.S.C. 154(b) by 0 days.

(21) Appl. No.: 18/298,244

(22) Filed: Apr. 10, 2023

(65) Prior Publication Data
US 2023/0240604 A1   Aug. 3, 2023

Related U.S. Application Data

(63) Continuation of application No. 16/758,809, filed as application No. PCT/US2018/057338 on Oct. 24, 2018, now Pat. No. 11,622,718.
(Continued)

(51) Int. Cl.
*A61B 5/00*  (2006.01)
*A61B 5/0205*  (2006.01)
(Continued)

(52) U.S. Cl.
CPC .......... *A61B 5/6802* (2013.01); *A61B 5/0006* (2013.01); *A61B 5/02055* (2013.01); *A61B 5/021* (2013.01); *A61B 5/02405* (2013.01); *A61B 5/02416* (2013.01); *A61B 5/0261* (2013.01); *A61B 5/029* (2013.01); *A61B 5/0816* (2013.01); *A61B 5/11* (2013.01); *A61B 5/14551* (2013.01); *A61B 5/266* (2021.01); *A61B 5/352* (2021.01); *A61B 5/4812* (2013.01);
(Continued)

(58) Field of Classification Search
CPC . A61B 5/6802; A61B 5/0006; A61B 5/02055; A61B 5/021; A61B 5/02405; A61B 5/02416; A61B 5/0261; A61B 5/029; A61B 5/0816; A61B 5/11; A61B 5/14551; A61B 5/266; A61B 5/352; A61B 5/4812; A61B 5/6844; A61B 2560/0214; A61B 2562/0219; A61B 2562/028; A61B 2562/164; A61B 5/0008; A61B 5/01; A61B 5/024; A61B 5/061; A61B 5/14507; A61B 5/4806; A61B 5/6823; A61B 5/6833; A61B 5/02; A61B 5/0205; H04B 1/385; H04B 2001/3894; H04W 12/06
See application file for complete search history.

(56) References Cited

U.S. PATENT DOCUMENTS 7,604,603 B2   10/2009  Sackner et al.
8,545,416 B1   10/2013  Kayyali et al.
(Continued)

*Primary Examiner* — Jonathan T Kuo
(74) *Attorney, Agent, or Firm* — Shay Glenn LLP

(57) ABSTRACT

A wearable device and methods for providing a wearable device are disclosed. In a first aspect, the wearable device comprises at least one power source, one computer controller and a plurality of instruments that when worn on a user access physiological data from at least the user axilla. The wearable device monitors one or more or a combination of body temperature, pulse, R-R interval, respiration rate, pulse ox (SpO2), sleep, movement included fall detection. The device stores, processes and communicates collected or processed data to an external computer system. A software system provides summary information, reporting and alarms based on data collected by the one or more instruments.

20 Claims, 17 Drawing Sheets

Related U.S. Application Data

(60) Provisional application No. 62/576,546, filed on Oct. 24, 2017.

(51) Int. Cl.

| | | |
|---|---|---|
| *A61B 5/021* | (2006.01) | |
| *A61B 5/024* | (2006.01) | |
| *A61B 5/026* | (2006.01) | |
| *A61B 5/029* | (2006.01) | |
| *A61B 5/08* | (2006.01) | |
| *A61B 5/11* | (2006.01) | |
| *A61B 5/1455* | (2006.01) | |
| *A61B 5/266* | (2021.01) | |
| *A61B 5/352* | (2021.01) | |
| *H04B 1/38* | (2015.01) | |
| *H04B 1/3827* | (2015.01) | |
| *H04W 12/06* | (2021.01) | |

(52) U.S. Cl.
CPC ........... *A61B 5/6844* (2013.01); *H04B 1/385* (2013.01); *H04W 12/06* (2013.01); *A61B 2560/0214* (2013.01); *A61B 2562/0219* (2013.01); *A61B 2562/028* (2013.01); *A61B 2562/164* (2013.01); *H04B 2001/3894* (2013.01)

(56) References Cited

U.S. PATENT DOCUMENTS

| | | | |
|---|---|---|---|
| 9,164,000 B2 | 10/2015 | Augustine | |
| 10,285,617 B2 | 5/2019 | Toth et al. | |
| 10,973,422 B2* | 4/2021 | Pantelopoulos | A61B 5/02438 |
| 11,622,718 B2* | 4/2023 | Vorster | A61B 5/02405 |
| | | | 600/301 |
| 2004/0170216 A1 | 9/2004 | Russak et al. | |
| 2009/0076340 A1* | 3/2009 | Libbus | A61B 5/11 |
| | | | 600/509 |
| 2012/0029310 A1 | 2/2012 | Paquet et al. | |
| 2014/0232516 A1 | 8/2014 | Stivoric et al. | |
| 2016/0183794 A1 | 6/2016 | Gannon et al. | |
| 2016/0267172 A1 | 9/2016 | Cole et al. | |
| 2016/0324487 A1* | 11/2016 | Guo | A61B 5/0816 |
| 2017/0156594 A1* | 6/2017 | Stivoric | A61B 5/0008 |
| 2017/0209055 A1* | 7/2017 | Pantelopoulos | A61B 5/02108 |
| 2017/0231490 A1* | 8/2017 | Toth | G16H 40/63 |
| | | | 600/558 |

\* cited by examiner

Pediatric Ward +Add Patient Alerts Menu

Vitls

* Unstable 2 of 27 Patients

| Room 2 Bed 3 504 | Name |
|---|---|
| PULSE SATS RESPIRATION TEMP | |
| 130  99% 506 27 508 98 | |
| BPM SpO₂  BrPM  F | |

| Room 3 Bed 2 | Name |
|---|---|
| PULSE SATS RESPIRATION TEMP | |
| 130  99%  27  98 | |
| BPM SpO₂  BrPM  F | |

* At-Risk 2 of 27 Patients

| Room 1 Bed 1 | Name |
|---|---|
| PULSE SATS RESPIRATION TEMP | |
| 122  99%  27  98 | |
| BPM SpO₂  BrPM  F | |

| Room 1 Bed 1 | Name |
|---|---|
| PULSE SATS RESPIRATION TEMP | |
| 122  99%  27  98 | |
| BPM SpO₂  BrPM  F | |

* Stable 23 of 27 Patients

| Room 1 Bed 1 | Name |
|---|---|
| PULSE SATS RESPIRATION TEMP | |
| 130  99%  24  98 | |
| BPM  BrPM  F | |

| Room 1 Bed 2 | Name |
|---|---|
| PULSE SATS RESPIRATION TEMP | |
| 110  99%  24  98 | |
| BPM  BrPM  F | |

| Vitals | Pediatric Ward | 📶 ◻ 12:38 |
|---|---|---|
| * stable | +Add Patient | 🔔 ≡ Alerts Menu |

| Room 1 Bed 1 | Name | Room 1 Bed 2 | Name |
|---|---|---|---|
| PULSE SATS RESPIRATION TEMP | | PULSE SATS RESPIRATION TEMP | |
| 110 99% 26 98.6 | | 110 99% 27 98.6 | |
| BPM SpO₂ BrPM F | | BPM SpO₂ BrPM F | |

| Room 1 Bed 3 | Name | Room 1 Bed 4 | Name |
|---|---|---|---|
| PULSE SATS RESPIRATION TEMP | | PULSE SATS RESPIRATION TEMP | |
| 110 99% 28 98.6 | | 110 99% 27 98.6 | |
| BPM SpO₂ BrPM F | | BPM SpO₂ BrPM F | |

| Room 2 Bed 1 | Name | Room 2 Bed 2 | Name |
|---|---|---|---|
| PULSE SATS RESPIRATION TEMP | | PULSE SATS RESPIRATION TEMP | |
| 130 99% 24 98.6 | | 130 99% 24 98.6 | |
| | F | | F |
| Room 2 Bed 2 | Name | Room 4 Bed 4 | Name |

Vitals | PULSE Room 1 Bed 2 | SATS Room 1 Bed 2 | RESP Room 1 Bed 2 | TEMP Room 1 Bed 2 | +Add Patient | Alerts | Menu

Pediatric Ward

✱ Unstable — 8 Active Alert

| Room 2  Bed 3 | Name |
|---|---|
| PULSE  SATS  RESPIRATION  TEMP | |
| 130  99%  27  98.6 | |
| BPM  %SpO₂  BrPM  F | |

| Room 3  Bed 2 | Name |
|---|---|
| PULSE  SATS  RESPIRATION  TEMP | |
| 130  99%  27  98.6 | |
| BPM  %SpO₂  BrPM  F | |

✱ At-Risk — 8 Active Alert

| Room 1  Bed 1 | Name |
|---|---|
| PULSE  SATS  RESPIRATION  TEMP | |
| 122  99%  27  98.6 | |
| BPM  %SpO₂  BrPM  F | |

| Room 1  Bed 1 | Name |
|---|---|
| PULSE  SATS  RESPIRATION  TEMP | |
| 122  99%  27  98.6 | |
| BPM  %SpO₂  BrPM  F | |

✱ Stable

| Room 1  Bed 1 | Name |
|---|---|
| PULSE  SATS  RESPIRATION  TEMP | |
| 130  99%  24  98.6 | |

| Room 1  Bed 2 | 8 Add Notes |
|---|---|
| PULSE  SATS  RESPIRATION  TEMP | |
| 110  99%  24  98.6 | |

SELF CONTAINED MONITOR AND SYSTEM FOR USE

CLAIM OF PRIORITY

This application is a continuation of U.S. application Ser. No. 16/758,809, filed Apr. 23, 2020, which is a 371 of PCT/US2018/057338, filed on Oct. 24, 2018, which claims the benefit of U.S. Provisional Patent Application No. 62/576,546, filed on Oct. 24, 2017, the entire disclosures of which are incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

STATEMENT AS TO FEDERALLY SPONSORED RESEARCH

This invention was not made with U.S. Federal Government support.

FIELD

This application relates to monitoring devices useful for detecting, storing, processing or communicating one or more physiologic parameters of the human or animal wearing the monitoring device.

BACKGROUND

Despite recent advancements in wearable device technology, there remains a need for improvements in the field to provide better remote user monitoring.

SUMMARY OF THE DISCLOSURE

In a first aspect, a wearable device is provided. The wearable device is removably attachable to a user to position a plurality of different instruments into a detection envelope of a user. The wearable device comprises an enclosure having a first end, a second end and a flexible portion extending between the first end and the second end; a plurality of instruments within the first end and the second end. The detection envelope is a portion of an axilla of the user.

In some embodiments, the length of the flexible portion is sufficient to place the one or more instruments in the first end of the enclosure over a portion of the thoracic cavity of the user while the second end of the enclosure is on or near or within detectable range of the vessels, nerves or the axilla of the user. At least a portion of the second end of the enclosure can be adapted and configured or shaped so as to correspond to one or more than one anatomical landmark or feature of the axilla so as to aid in the correct placement of the wearable device for monitoring one or more physiological parameters of the use detectable from the site in the axilla of the user. In some embodiments, the second end comprises an indicator adapted to be used to positioned the device relative to one or more anatomical landmark or feature of the axilla.

The power source for the wearable device operation can be located in one of the first end of the housing, the second end of the housing or the flexible portion of the housing.

In some embodiments, a battery is located in a portion of the wearable device where another portion of the wearable device is disposed partially or completely between the bottom of the battery and the skin of the user. The battery can be located in an upper most portion of the wearable device. In some embodiments, the battery is a flexible battery that bends along with the bending of the flexible portion when in use on the user. The battery can be rechargeable by non-contact recharging methods. In some embodiments, the battery may power the wearable device for more than 70 hours of continuous monitoring of the user using one or more instruments in the enclosure. The battery can power the wearable device for more than 140 hours of continuous monitoring of the user using one or more instruments in the enclosure. In some embodiments, the device comprises one or more of an antenna, a microcontroller, a microelectromechanical system (MEMS), and a wireless transceiver. The power source or battery can be selected from the group consisting of a rechargeable battery, a coin battery, a button battery, a flexible battery, an energy harvesting unit, and a solar cell, further wherein the at least one power source is coupled to the first module via the first PCB.

In some embodiments, the device comprises an upper foam layer, or a bottom foam or a foam layer comprising a hydrogel layer that includes an adhesive. There can be one or more of a PCB within the enclosure and the PCB is selected from the group consisting of a soft PCB, a flexible PCB, and a stretchable PCB to provide wear comfort. In some embodiments, the first end comprises a rigid PCB. The second end can comprise a rigid PCB. In some embodiments, the flexible portion comprises a flexible PCB. The device can comprise a dogbone shape. In some embodiments, the flexible portion comprises a thickness less than about 0.3 mm. The flexible portion can comprise a modulus of about 17,000 kpsi.

In some embodiments, the device comprises an optical array adapted to monitor at least one physiological parameter of the user. The device can comprise secondary instruments configured to collect data to assist in calculations of physiological parameters. In some embodiments, the device comprises an accelerometer. The flexible portion can be adapted for performing data transfer between the first and second ends of the device. In some embodiments, the first end is larger than the second end.

The device can comprise a communication module. The device can comprise a RF module. In some embodiments, the first end comprises a communications module.

The device can be configured to monitor at least one of the following physiological parameters: body temperature, heart rate, heart rate variability, RR interval, respiration rate, blood oxygen levels (SpO2), blood pressure, cardiac output, body fluid analysis, sleep cycles, movement and proximity of the device to the skin of the user.

In some embodiments, the device is configured to transmit data to a nearby bridge device. The bridge device can comprise a communication module. In some embodiments, the bridge devices comprises machine executable instructions configured to cause the bridge device and the wearable device to pair. The bridge device can be configured to communicate using at least one of wifi/Ethernet/mobile, Bluetooth, RF. In some embodiments, the bridge device comprises machine executable instructions configured to cause the bridge device to authenticate the wearable device prior to pairing. The bridge device can comprise machine executable instructions configured to send data received from the wearable device to a cloud database. In some embodiments, the bridge device comprises machine executable instructions configured to send data received from the wearable device to a hospital station.

In some embodiments, the enclosure is waterproof. The device can comprise a power control. In some embodiments, the device is configured to being monitoring upon being turned on or upon a specific pre-programmed motion. The device can be configured to be programmed wirelessly or using a programmer unit.

In some embodiments, the device is configured to monitor cardiac output through pulse contour analysis. The device can be adapted and configured for collection of physiological parameters of the user wherein at least one instrument portion of the wearable device is configured for placement within the axilla of a user. In some embodiments, the instrument portion configured for placement for registering user parameters via the axilla may have an outward size, shape, contour or surface configured for user comfort based on the overall profile, shape, size, flexibility, contour or other feature or characteristic of the wearable device to provide user comfort when positioned against the skin in a portion of the axilla and between the axilla and the arm, including when the in a lowered position against the axilla or when the arm is swinging relative to the axilla such as when walking or running or playing a sport or swimming, or other activities, including during recovery from a surgical procedure. The device can have the various instruments, microelectronics, communication components and power supply fully contained within the enclosure.

In some embodiments, the device comprises openings in the bottom or user facing surfaces of the enclosure provide access to or physical contact with the skin of the user. A skin contacting portion of a sensor instrument may extend below a bottom most surface of the enclosure. In some embodiments, the bottom most portion is a bottom surface of the enclosure. The bottom portion can be the bottom most portion of an adhesive affixed to the lower most portion of the enclosure. In some embodiments, the instrument contacting portion of the instrument may extend 0.1 mm, 0.2, mm, 0.3 mm, 0.4 mm, 0.5 mm, 0.6 mm below the bottom portion. The user can be an obese user and the amount of the instrument extending below the bottom surface may be adjusted in response to the amount of fat in the axilla of the obese user wherein in use the instrument is able to detect the physiological parameters of the obese user. In some embodiments, the wearable device top layer of the enclosure is made of foam and the bottom layer is a combination of a plastic film and silicone adhesive.

The adhesive can be only applied to the bottom surface of the perimeters of the ends of the device. In some embodiments, the adhesive is applied along the entire bottom surface of the enclosure in contact with the skin of the user or the adhesive is present on the bottom surface of the end portions of the wearable device, along the perimeter with at least one, more than one or a series of gaps in the adhesive to increase user comfort. The edge of the enclosure and the adhesive can have a sloped shape to reduce the profile of the device or with other shapes to increase user comfort or the outer surface of the enclosure, an upper or superior aspect of the enclosure, a lower or inferior aspect of the enclosure, a joining or transition section of the flexible portion to an end portion are shaped, sized, configured, contoured, textures, treated, beveled or otherwise modified to increase user comfort or increase the conformability of the wearable device to the anatomical site where the device will be releasable affixed to the user or to increase the conformity of the device to a portion of the skin of the user, a portion of the axilla of the user, a portion of a posterior aspect of the user's chest or a portion of an anterior aspect of the user's chest or other shape to conform with all or a portion of an anatomical site where the wearable device will be placed on the user.

The central portion can have a nearly constant width from one end to the other end of the wearable device or the central portion has a wider portion nearer one end of the wearable device or the central portion of the wearable device has a decreasing width towards the portion of the device contacting the user axilla. In some embodiments, the overall length of the device is sufficient to have one end and the associated instruments within the axilla and the other end and any associated instruments outside of the axilla, or outside of the axilla on an anterior or posterior aspect of the thoracic cavity of the user or the overall length of the wearable device is more than 115 mm or the overall length of the wearable device is more than 145 mm or the overall length of the wearable device is from about 110 mm to about 150 mm or the overall length of the wearable device from about 135 mm to about 160 mm or up to 170 mm, up to 180 mm, up to 190 mm, or 200 mm. The area of one end of the device can be larger than the area of the other end of the device or a larger end of the device can have an area of 350-700 square mm or the smaller end of the device has an area of 150-350 square mm or the central portion between the ends is from 70 to 90 mm or the central portion between the two ends is from 90 to 130 mm or the central portion can be sized for an obese user or the length of the central portion is 140 mm, 150 mm or 160 mm.

The device can have any one or a combination of electronics completely within the enclosure, and/or, portions of the electronics may be positioned into optimized locations based on use or function with other components of the wearable device or a data input port is placed towards the central portion of the device towards the flexible central portion to shorten the length of a data line from the one or more instruments on the other end of the flexible middle portion. In some embodiments, an output or an indicator of the electronics system may be positioned in proximity to the instrument collecting the data to be displayed again to make the device more compact by shortening data and sensing lines and circuitry or permitting even more compact ASIC device designs and/or wherein one temperature instrument is adjacent or proximate to an external temperature instrument that provides an output visible when viewing an outer surface of the enclosure or, wherein the temperature instrument can be positioned on the smallest end portion of the device and/or wherein an output based on data collected by one or more temperature instruments of the wearable device is visible on a portion of the device designed for placement within an axilla of the user and/or wherein there can be a temperature instrument on the wearable device and the computer controller or microprocessor of the wearable device includes computer readable instructions for obtaining a temperature reading from the instrument or for basing a temperature output to a device indicator by processing the output of the temperature instrument.

In some embodiments, the wearable device contains within the enclosure a plurality of instruments that when the device is positioned with one end in a portion of the axilla of a user, the electronics and the power supply of the wearable device are outside of the axilla or all or a portion of a power supply may be within the portion of enclosure within a portion of the axilla. The wearable device can contain within the enclosure a plurality of instruments that when the device is positioned with one end in a portion of the axilla of a user, the electronics and the power supply of the wearable device are outside of the axilla within the bendable central portion and the other end of the wearable device enclosure or all or a portion of a power supply may be within the bendable central portion of enclosure.

The device can comprise a memory including computer readable instructions for one or more of: collecting, processing or storing within the memory of the wearable device signals from the one or more instruments on the wearable enclosure; methods for compressing the data within the memory; methods for electronic transmission to a computer system electronically linked to wearable device; algorithms specific to the instrument type, data collection type, user physiological parameter being monitored, measured, collected or processed by the wearable device; and any specific factors, variables, calibration information, software, firmware or middle ware for recommended or specifically configured use of a temperature instrument, an ECG instrument, a next-generation optical instrument including infrared, red and green portions of the spectrum, a PPG instrument, an instrument having an LED based instrument, a micro machined (MEMS) or nanotechnology instrument (Nano sensor) or other component within the enclosure that when worn by a user detects one or more physiological parameters of the user.

In some embodiments, the enclosure contains an appropriately situated PPG instrument and the memory of the instrument controller or microcontroller contains computer readable instructions for conducting Photo plethysmography processing of outputs from the PPG instrument to monitor at least pulse, R-R interval, respiration rate and blood oxygen, alone or in combination or consideration of contemporaneously collected, sequentially collected or simultaneously collected instrument data from another instrument on the wearable device. The wearable device can comprise one or more of a suitable communications component to transfer data collected by the instruments, processing results from the electronics, data stored within the memory of the device or any other electronic signal collected or produced by the device to an external site including another computer whether connected by local network as in a hospital setting or via suitable connection to a cloud based or remote networked location or to a tablet, smart phone, or other mobile device adapted or configured via app or other software for communication with the wearable device.

A software based system for communicating with a wearable device as described herein is provided. The system can be adapted to receive, store, process, and transmit data or information from one or more wearable devices and/or for generating status, warning, or other information about a user wearing a wearable device.

A base unit having a computer controller with computer readable instructions for operating the software based system can be provided. The controller can have computer readable instructions for electronic communications with any of the wearable device described herein.

An app, desktop or web based software program for use with a smart phone, tablet, mobile device, or computer adapted and configured for electronic interaction can be provided. The app, desktop or web based software program can comprise a dashboard view configured to display data received from a plurality of wearable devices. In some embodiments, the app, desktop or web based software program comprises a patient view configured to display data received from a single wearable device. The app, desktop or web based software program can be configured to allow a clinician to set upper and or lower limits for a monitored parameter. In some embodiments, the app, desktop or web based software program is configured to produce an alert when a monitored parameter is outside the range set by the upper and lower limits. The app, desktop or web based software program can be configured to group patients into sections. In some embodiments, the app, desktop or web based software program is configured to color code displayed parameters based on the parameters meeting set thresholds.

In another aspect, a method of monitoring a user is provided, the method comprising removably attaching a device to the skin of a user, the device comprising a first end and a second end connected by a flexible portion and arranged in a dogbone shape; monitoring one or more physiological parameters of the user, including at least one of body temperature, heart rate, heart rate variability, RR interval, respiration rate, blood oxygen levels (SpO2), blood pressure, cardiac output, body fluid analysis, sleep cycles, movement and proximity of the device to the skin of the user; and executing machine executable instructions configured to cause the device to send user data to a remote database.

The method can comprise attaching a portion of the second end to an axilla of the user. In some embodiments, the method comprises using an indicator on the second end to position a portion of the second end on an axilla of the user. The method can comprise monitoring cardiac output using data received from the pulse sensor. In some embodiments, the method comprises entering user data into an app configured for electronic interaction with the device. The method can comprise pairing the device with a base station using the app. In some embodiments, the method comprises executing machine executable instructions configured to cause the device to transmit data to the base station. The method can comprise executing machine executable instructions configured to cause the app to prompt a clinician to confirm a location of the device. In some embodiments, the method comprises executing machine executable instructions configured to cause the app to prompt a clinician to confirm a location of the device if any data value remains null for more than a set amount of time.

In another aspect, a device for noninvasively measuring cardiac output of a user is provided. The device comprises a first end and a second end connecting by a flexible portion; an optical sensor located on the second end and configured to be positioned on or near an axilla of the user; a communication module on the device configured to send data received from the optical sensor to a remote device or computer; and a processor configured to calculate the cardiac output based on data received from the optical sensor.

In yet another aspect, a method for noninvasively measuring cardiac output is provided. The method comprises placing a device comprising a first end and a second end connected by a flexible portion on the user; positioning the device so that an optical sensor on the second end is positioned on or near the axilla of the user; monitoring physiological parameters using the optical sensor; sending data from the optical sensor to a remote device or database; and calculating the cardiac output from data received from the optical sensor.

BRIEF DESCRIPTION OF THE DRAWINGS

The novel features of the invention are set forth with particularity in the claims that follow. A better understanding of the features and advantages of the present invention will be obtained by reference to the following detailed descrip

FIGS. 5-11 illustrate various embodiments of screens within an app usable with a wearable device.

DETAILED DESCRIPTION

Described herein are various embodiments of wearable devices designed to measure physiological parameters such as body temperature, pulse, and respiration. The devices can provide constant monitoring of hospital patients, reducing workload and human error caused by overworked clinicians. The devices can also provide accurate monitoring while allowing users comfort and ability to move more than traditional sensor devices. Further details and advantages provided by the devices are described herein.

Figure 1A:
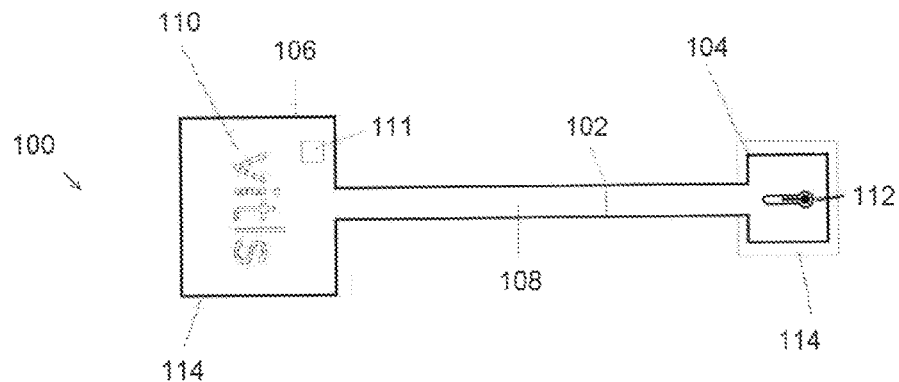
- FIGS. 1A and 1B show an embodiment of a wearable device.
Figure 1B:
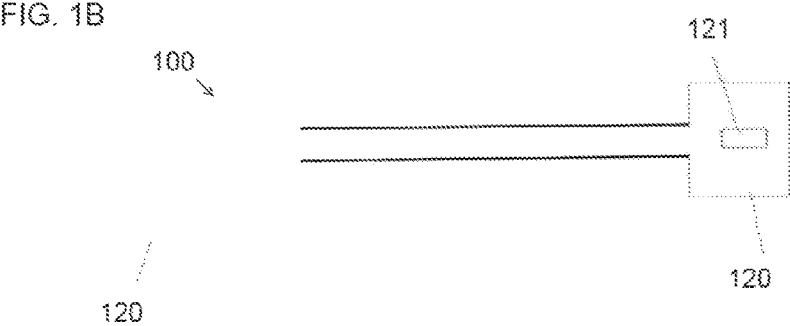

In some embodiments, the device has a dog bone shape, wherein a width of a first and second end of the devices is greater than the width of a central portion of the device. One such embodiment is the sensor shown in FIGS. 1A-2B. FIG. 1A shows a top view of an embodiment of the device 100. The device comprises a first end or main board 106 and a second end or device board 104 connected by an intermediate portion or flex board 108. FIG. 1B shows a bottom view of the device 100. A dogbone shape can help to maximize flexibility/bendability and also ensure that these devices are comfortable and unobtrusive to wear. Dimensions and weight can also be kept to a minimum for this same reason. The device can be thin, flexible, unobtrusive and comfortable to wear in order to mitigate the risk of irritation or inconvenience, especially in the case of pediatric users. The corners of the circuit boards have been rounded in order to prevent damage to the enclosure. The device 100 can comprise a thin bevel 114 to reduce edges and increase user comfort.

Figure 3:
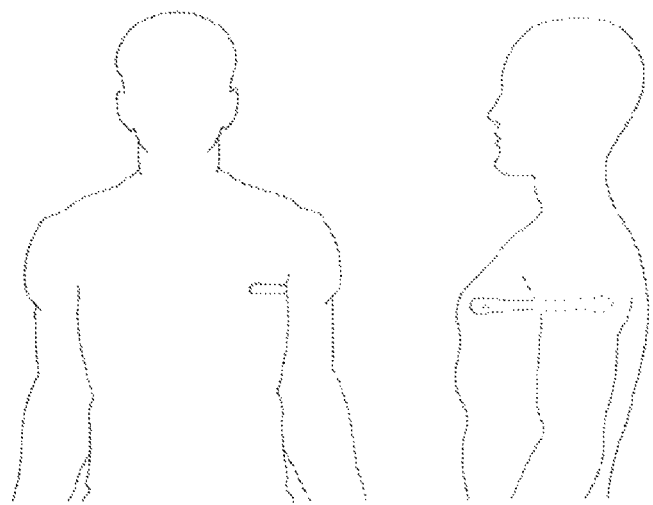
FIG. 3 depicts an embodiment of a wearable device positioned on a user.
Figure 12:
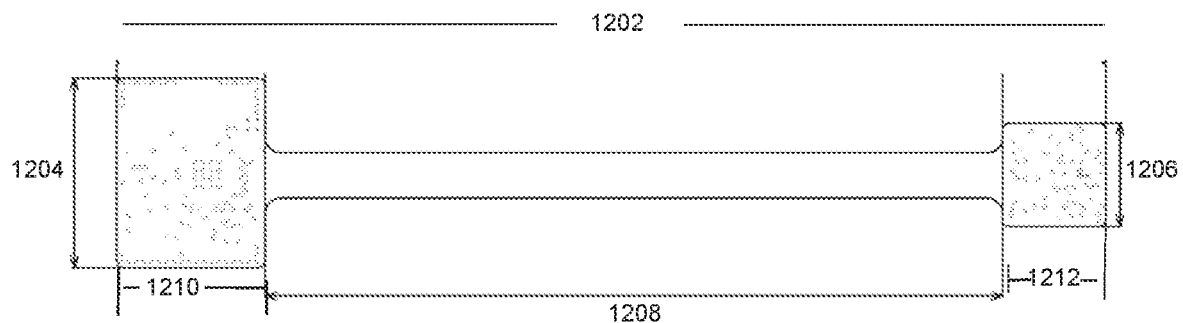
FIG. 12 depicts an embodiment of a wearable device showing various dimensions.
Figure 13:
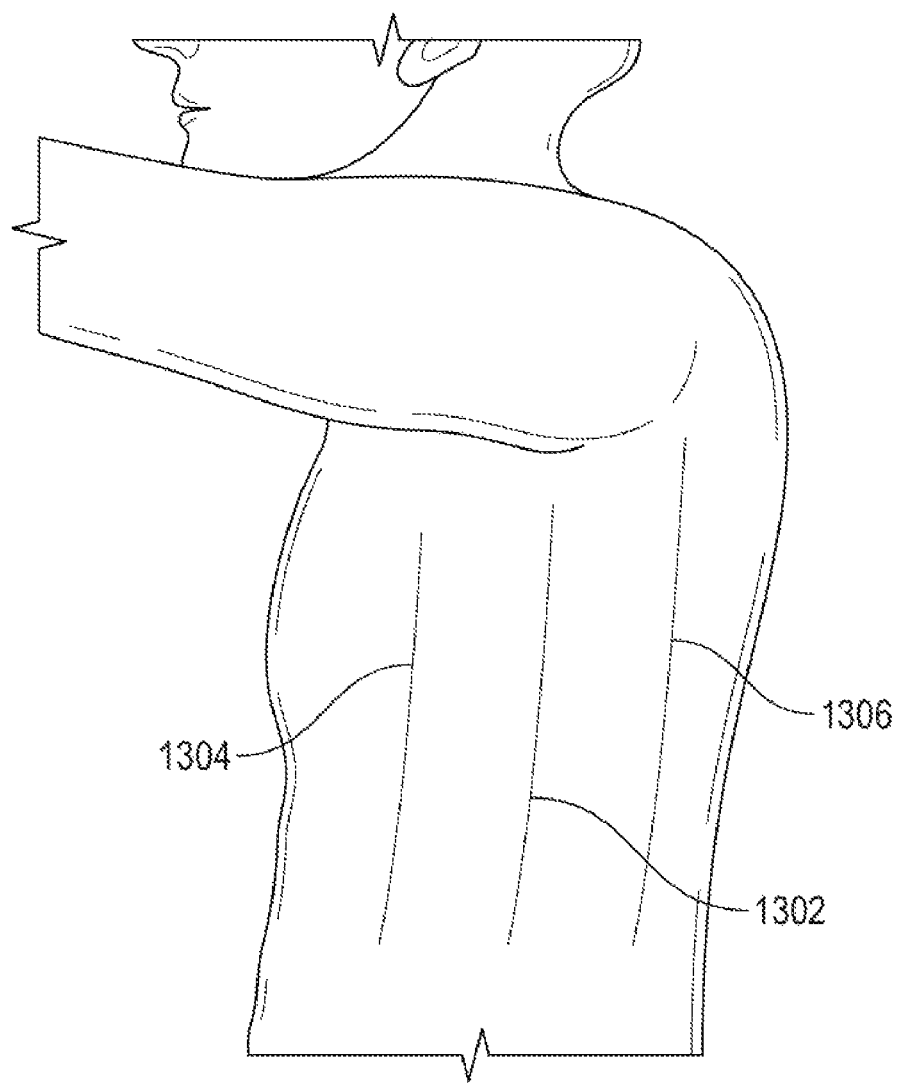
FIG. 13 shows a midaxillary line on a person.

The device can utilize thin circuit boards to keep overall thickness as low as possible. In all embodiments, a flexible, semi-rigid or rigid PCB or circuit board is used. A flexible circuit board conforms to the user's skin which reduces irritation for the user and stresses on the device enclosure and adhesives. In certain embodiments, a flex board (the flex strap or central portion) connects the two circuit boards. This is a reliable way to connect the two boards and ensure the connection remains intact during wear. The flex board 108 can be less than about 0.3 mm thick and be extremely flexible. Weight can be kept to a minimum to increase comfort and decrease stresses on the adhesive on the user's skin. As shown in the bottom view of FIG. 1B, the adhesives 120 may be located on the ends of the device and not on the flexible strap that connects the boards. This can help to ensure unencumbered movement. The adhesive design assists with breathability to reduce the risk of skin irritation/atrophy. The adhesive is positioned around the devices as to not interfere with monitoring. An optical array 121 for monitoring various physiological parameters of the user can be positioned on the device board 104. The optical array consists of multiple emitters (red, green, infrared), detectors and a light barrier to block optical crosstalk. The enclosure of the device 100 can be made of a bio-compatible material that is comfortable to wear and extremely light weight. In the exemplary embodiments described herein, the device has been designed in two different sizes, one for pediatric patients and one for adult patients. The length from the Midaxillary Line 1302 (FIG. 13) to the chest differ in children and adults, which is the reason for the two sizes. For placement of the device Board, 104, the Midaxillary Line Indicator 112 on the device should preferably be located on, or as near as possible to the Midaxillary Line of the user (FIG. 13). For placement of the Main Board 106 end, the Main Board should preferably extend onto the chest, vertically in line (above) or past the nipple, as shown in FIG. 3. A logo 110 or other indicator can be used to indicate the main board. The main board 106 can include a power button 111. An indicator, such as a thermometer 112, can be used to indicate the device board and be used to aid in positioning. In other embodiments, the line indicator 102 can be used for positioning. In other embodiments, the device can be lined up using the anterior axillary line 1304 or posterior axillary line 1306. Measuring instruments can be placed on the device board 104, located in the armpit, in order to measure various physiological parameters such as heart rate, pulse oximetry, blood pressure, cardiac output (through pulse contour analysis), body temperature and respiration rate. These devices can be placed in the axilla, specifically, to mitigate the risk of optical interference from other light sources, provide more accurate readings and reduce motion artefact, which can result in inaccurate readings. Because of the significantly lower level of motion artefact, compared to the extremities, the chest has proven to be the ideal location to place this device. Secondary signals can be monitored using instruments like an accelerometer. These secondary signals are used to assist in calculations of parameters. Exemplary device dimensions are provided in the table below and with reference to FIG. 12 and for the pediatric device and the adult device, respectively.

In some embodiments, the device with the enclosure can comprise a length of about 100-140 mm (e.g., about 120 mm, about 110-130 mm, etc.) for the pediatric device and a length of about 120-170 mm (e.g., about 145 mm, about 130-150 mm, etc.) for the adult device. The device with enclosure can comprise a main board width of about 20-50 mm (e.g., about 35 mm, about 30-40 mm, etc.) The device with enclosure can comprise a device board width of about 10-30 mm (e.g., about 20 mm, about 15-25 mm, etc.). The device with enclosure can comprise a height of about 7-21 mm (e.g., about 14, about 11-17 mm, etc.)

In some embodiments, the device without enclosure can comprise a length 1202 of about 95-135 mm (e.g., about 114 mm, about 104-124 mm, etc.) for the pediatric device. The device without enclosure can comprise a length 1202 of about 1300-1380 mm (e.g., about 1344 mm, about 1320-1360 mm, etc.). The device can comprise a main board width 1204 of about 10-40 mm (e.g., about 25 mm, 15-35 mm, etc.). The device without enclosure can comprise a device board width 1206 of about 7-21 mm (e.g., about 14, about 11-17 mm, etc.). The device without enclosure can comprise a height of about 5-15 mm (e.g., about 10 mm, about 8-12 mm, etc.). The device without enclosure can comprise a center portion length 1208 of about 80-120 mm (e.g., about 100 mm, about 90-110 mm, etc.). The device without enclosure can comprise a main board length 1210 of about 10-30 mm (e.g., about 20 mm, about 15-25 mm, etc.). The device without enclosure can comprise a device board length 1212 of about 7-21 mm (e.g., about 14, about 11-17, etc.).

Figure 2A:
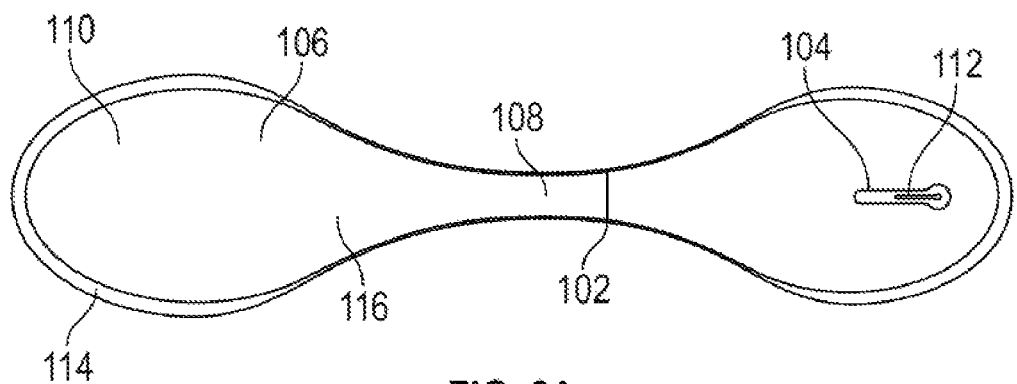
FIGS. 2A and 2B illustrate another embodiment of a wearable device.
Figure 2B:
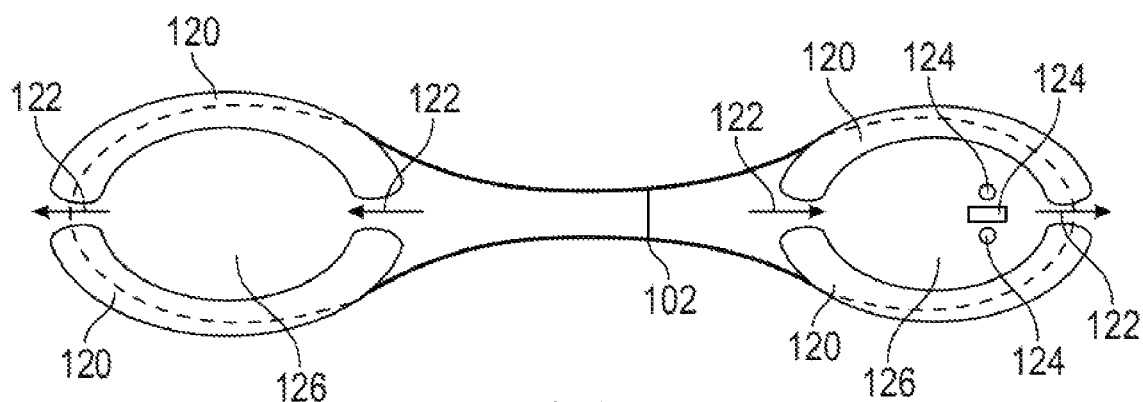
Figure 14:
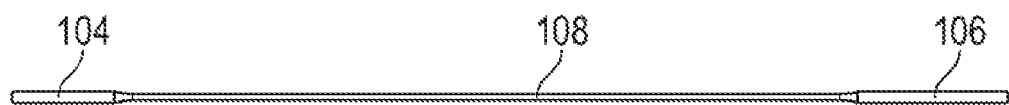
FIGS. 14-16 illustrate various views of an embodiment of a wearable device.
Figure 15:
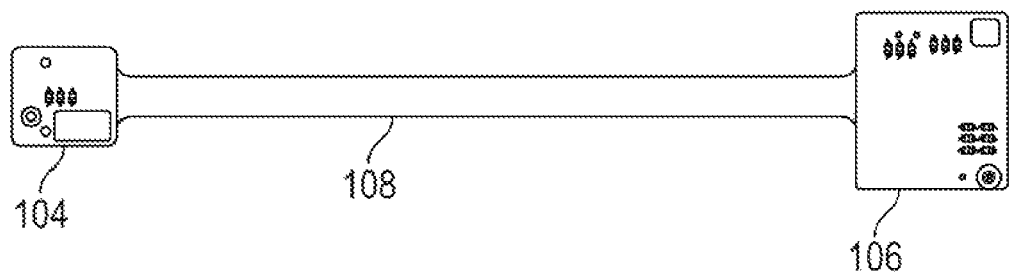
Figure 16:
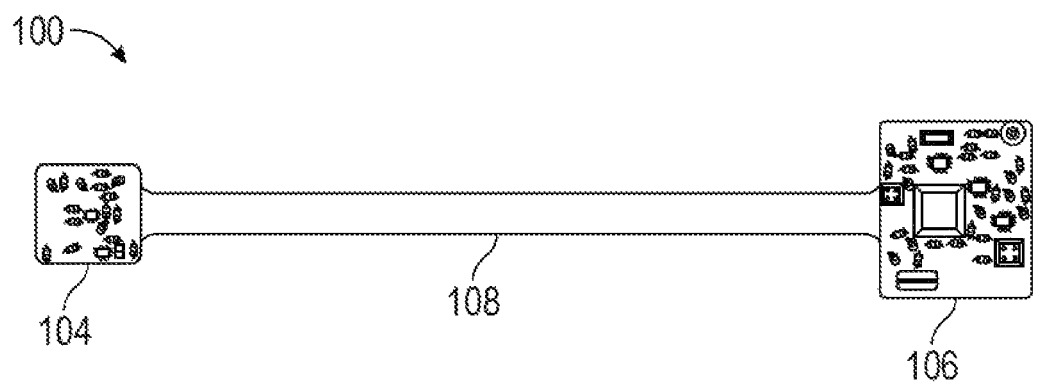

FIGS. 14, 15, and 16 show a side view, top view, and bottom view, respectively of an embodiment of a device 100, showing the flex board 108, the device board 104 and the main board 106. The device 100 can also incorporate a flexible battery, within the shape of the flex board 108, that conforms with the device around curve of the chest. The flexible middle section 108 is used for data transfer between the sensor board and the main board. The curve is needed to ensure maximum connectivity with the skin of the user and to reduce stresses on the adhesives (FIG. 2). The middle section can be flexible with a modulus of 17,000 kpsi. There are two rigid circuit boards, the Main Board and the device Board that are connected with a flex board. The main board and the device board can differ in size. The device board can be smaller because it resides in the armpit and a small size can ensure no discomfort to the user. The Main Board is larger in size and contains the RF module along with its antenna and ground plain which requires a large footprint for optimal operation.

The RF module can be purposefully allocated to the main board and not the instrument board, to ensure optimal signal quality and range. The devices can be encapsulated in a bio-compatible material 116 (e.g., foam/film/silicone/plastic) that is light-weight, comfortable, and waterproof.

The device can be purposefully designed to be worn on either the left side or the right side of the chest. Certain measuring instruments protrude through the encapsulation material to ensure optimal coupling with the skin while other measuring instruments are covered by the encapsulation material. The main board can be located on the chest, away from any obstructions to ensure optimal RF signal. The human body contains water which affects RF radiation patterns. This is why the Main Board that houses the RF module is located as far away from the armpit as possible. The device board is located in the Axilla/Armpit to monitor certain physiological parameters and has been designed to be positioned in the armpit whether the device is located on the right or the left side of the chest. Various methods of shielding have been used to ensure the measuring instruments are not at risk of any interference which may affect the quality of the signals collected.

Combinations of various primary and secondary measuring instruments can be located on the instrument board and the main board. These may include next-generation optical instruments, temperature instruments, accelerometers, piezoresistive instruments and instruments for fluid analysis. Enclosures can comprise a single, molded part or multiple parts, fused together. The device has been designed to operate in low- as well as high-stress environments, from hospitals to homes, to fighter jets and the battlefield.

Figure 18:
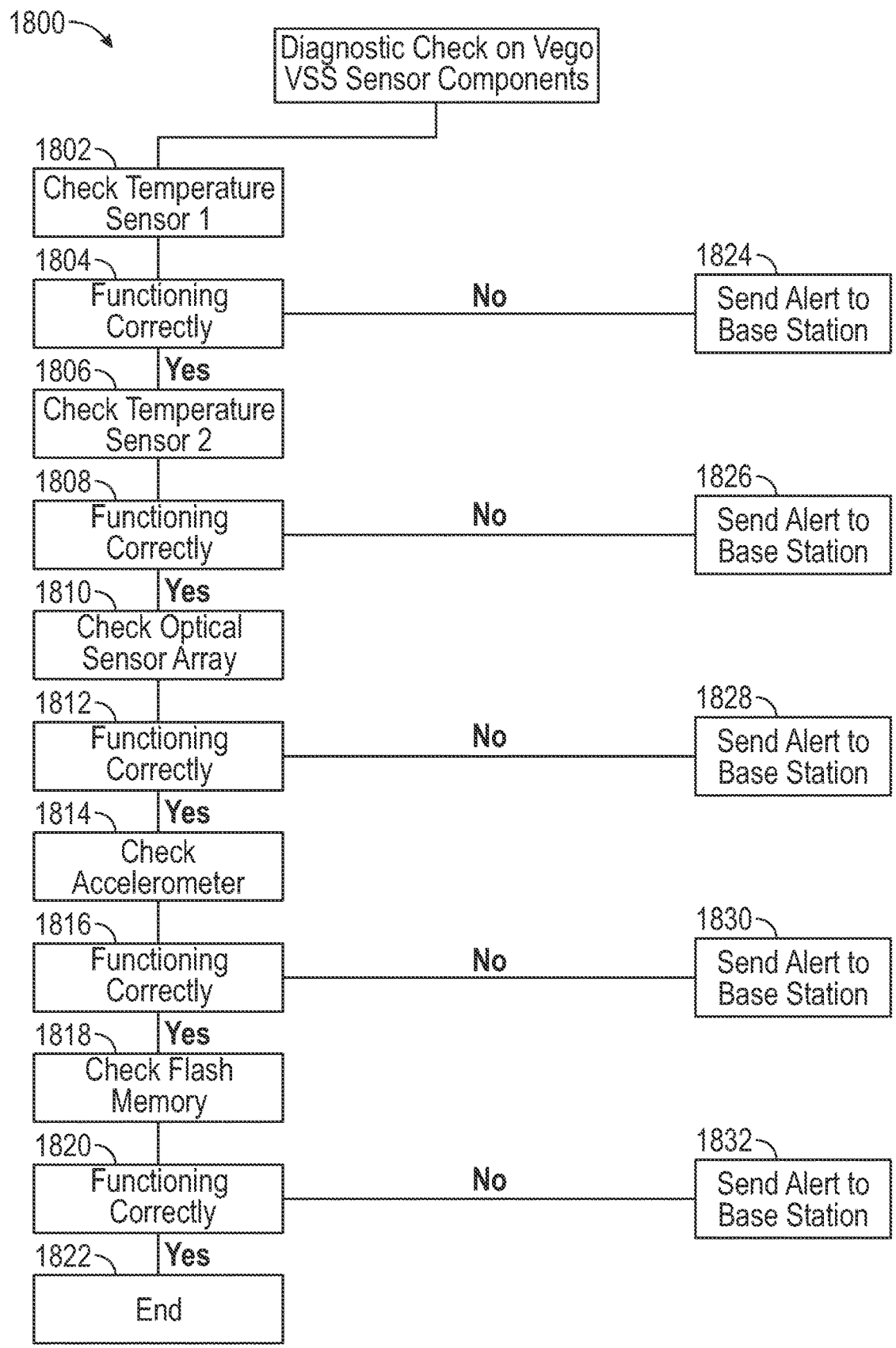
FIG. 18 shows an embodiment of a method of running a diagnostic check on a wearable device.

The device uses the above components, in various combinations, to monitor physiological parameters as well as other parameters. Among the parameters that could be collected are, body temperature, heart rate, heart rate variability, RR interval, respiration rate, blood oxygen levels (SpO2), blood pressure, cardiac output, body fluid analysis, sleep cycles, movement and proximity of the device to the skin of the user (if removed). Physiological signals are converted to actionable information, on the device and then transmitted. By continuously collecting the physiological and secondary signals of a user, a baseline (normal state) can be determined and by further, continuous monitoring, any deviation from that baseline could indicate an impending adverse event. This could provide valuable data to the user and prompt preventive measures that could reduce costs and health complications. Secondary signals can assist in the accuracy of the physiological signals, as well as indicate body position, when a user has fallen, for example, or how active a user has been during rehabilitation. The device can periodically run diagnostic checks to ensure that all components are functioning optimally (FIG. 18). Sampling rates can vary from 0.00333 hz (300 s (p)) to 300 hz (0.00333 s (p)). Data is transmitted to the bridge device at various intervals unless an alert occurs in which case transmission occurs immediately. When there is a loss of connection with the bridge device, the device can store the collected data, for up to 3 hours, until a connection with the bridge device has been re-established. To mitigate the risk of data breach, the device can only connect to one bridge device at a time. During connection, every device is authorized using a unique device identifier, hosted on a secure server. Security measures have been implemented to ensure the devices can only connect to the bridge device and the bridge device only accepts connections from authorized sensor devices.

In some embodiments, there is a bio-compatible adhesive to ensure minimal irritation and atrophy to the skin during wear. A repositionable adhesive has been chosen that allows the user to remove the device when going for an MRI or similar scan where foreign objects, that might interfere with the scan, are not allowed. The adhesives are only located underneath the main board and device board (FIG. 1B) of the device to keep contact between skin and adhesives to a minimum, thus further reducing the risk of irritation and atrophy. The adhesive also ensures that the device is closely coupled to the skin to not allow any movement, independent of the user's skin.

Figure 21A:
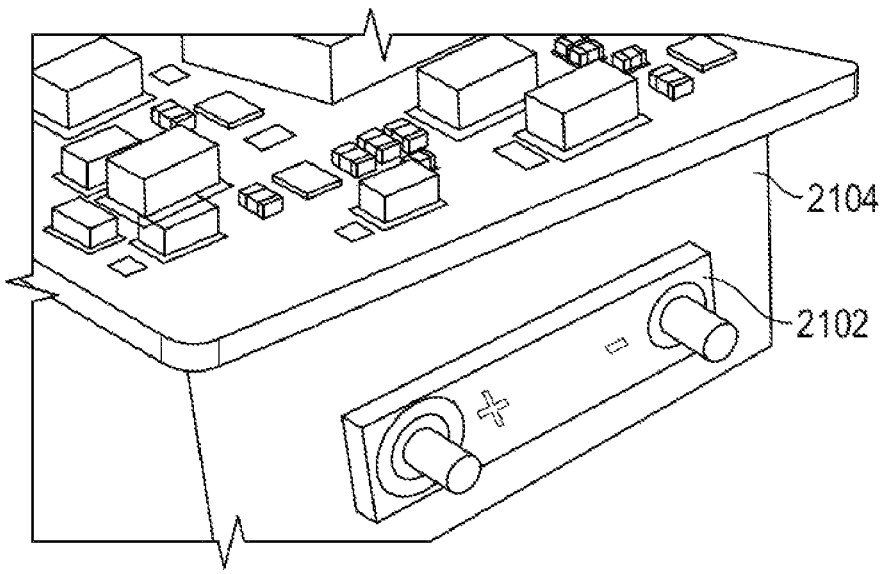
FIGS. 21A and 21B depict views of a battery positioned on a wearable device.
Figure 21B:
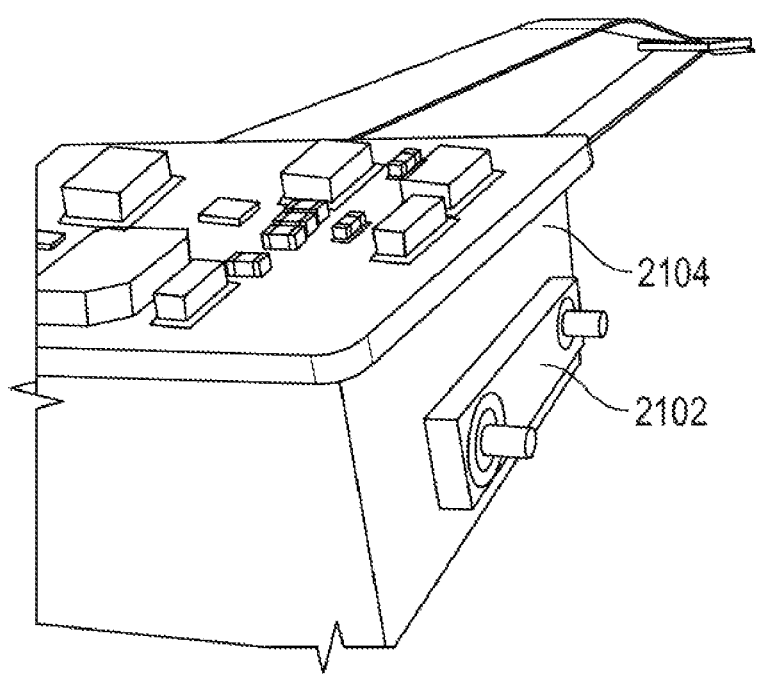

The device can be disposable and powered by a primary battery; or reusable and powered by a rechargeable battery. The battery can be recharged through induction, energy harvesting, daily activities using piezoelectric, thermoelectric and electromagnetic generators or wirelessly. In some embodiments the battery 2102 is connected to the board using a flexible circuit board tab 2104 as indicated in FIGS. 21A and 21B. Glue is used to adhere the battery to the circuit board. This mitigates the risk of unnecessary movement artefact caused by the battery moving around inside the device enclosure. The device also contains a PCB switch or button that can be triggered through the enclosure.

Figure 4:
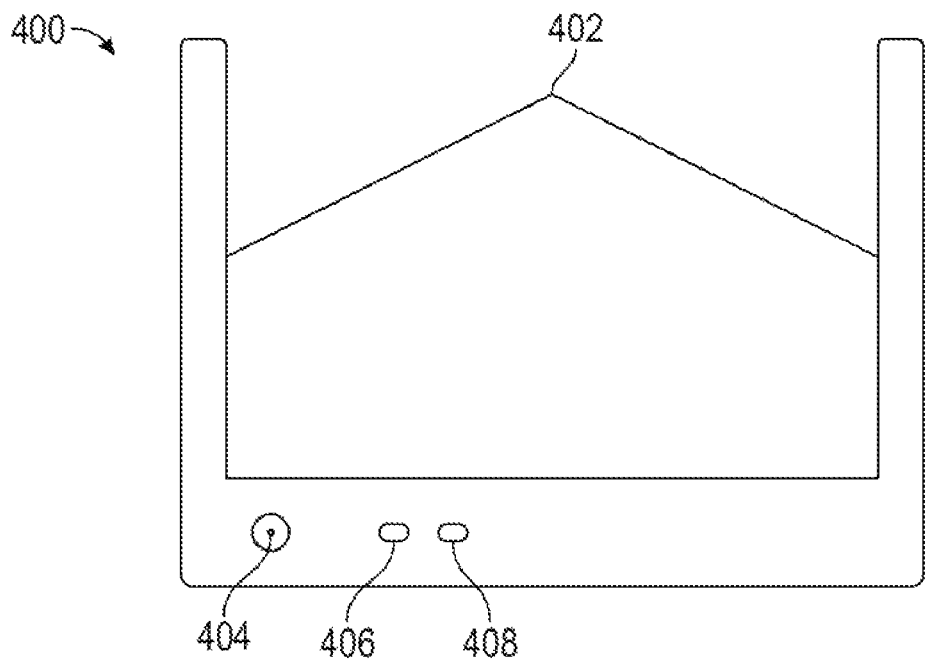
FIG. 4 shows an embodiment of a bridge device.

The skin of the user should be prepared before the device is attached. It has to be wiped with an alcohol swab and shaved to ensure maximum adhesion of the device. The device attaches to the user with the side displaying the temperature image on or as close as possible to the Midaxillary Line, lining up with the device's Temperature Image 112. The maxillary line may be used to align the device with any portion of the user axilla as defined elsewhere herein. The device is switched on and immediately establishes a secure connection with the nearest bridge device. FIG. 4 shows an example of a bridge device 400 comprising antennas 402, a power button 404, a power indicator (e.g., an LED) 406, and an internet connectivity indicator (e.g., an LED) 408.

The device has been designed to afford the user complete, unencumbered movement without being burdened by wires or bulky monitoring devices and without the accuracy being affected by the user's movement. The user can fall asleep on top of the device without experiencing any inconvenience. The enclosure is waterproof to allow the user to take a shower/bath without the need for removal. It can be a single use/disposable device (with a 6-day battery life) or it can be rechargeable either by harvesting energy from the user's body, by induction, wireless charging or other methods.

Monitoring starts as soon as the device has been switched on using a switch or specific, pre-programmed motion. (See FIG. 21). The device collects raw signals from the user which are processed by algorithms located on the device. The microcontroller contains instructions and processing modules to receive and process signals from specific instruments. The firmware manages the instrument processes as well as the Algorithms. The algorithms analyze the raw data that is collected by the devices. In some embodiments, for heart rate and RR interval, the optical sensor array collects data on capillary blood flow and the algorithms calculate the heart rate in beats per minute and RR interval in time between beats. For respiration rate the optical sensor array collects data on capillary blood flow which is combined with the accelerometer data on chest movement and the algorithms then calculate the respiration rate as breaths per minute. For pulse oximetry, the optical sensor array collects data on capillary blood flow and the algorithms calculate the % oxygen in the wearer's blood. The device firmware can be updated over the air, either through the bridge device 400 or a mobile device. Updates can also occur in real-time when pushed from a remote server. All the processed and raw data is batched and transmitted to the bridge device as required to optimize power usage. When an alert occurs though, data is not batched, but transmitted immediately.

It will be appreciated that the devices described herein can comprise any combination of the features described above with respect to any specific embodiment. Following are provided embodiments of devices comprising different combinations of features described herein.

In some embodiments, the wearable device measures body temperature, pulse and respiration. The device can incorporate various primary instruments (sensors) and secondary instruments, including an accelerometer, to calculate physiological parameters. The device can be constructed of two rigid circuit boards with a flex tape that connected the boards. The flex tape can be replaced with a different length of flex tape depending on the application—children or adults. The boards can be a compact design to ensure the device is small and unobtrusive to the use. The device can be programmable using a micro-USB cable and can be powered by any battery with a micro-USV connector. The device can contain one temperature instrument and an optical array. The RF antenna can be placed at the rear of the main board to mitigate the risk of interference from other components. The device can communicate with the bridge device using Bluetooth Low Energy (BLE).

In some embodiments, the wearable device measures body temperature, pulse and respiration. The device can incorporate various primary instruments (sensors) and secondary instruments, including an accelerometer, to calculate physiological parameters. The device can be constructed of a rigid-flex circuit board design. The flexible board can have a modulus of 17,000 kpsi. There can be two rigid circuit boards, the Main Board and the device Board that are connected with a flex board These two rigid boards at the ends of the device can differ in size. The boards can incorporate more components and measurement instruments, but still have a compact design to ensure the device is small and unobtrusive to use. This embodiment can be designed for placement within an axilla of the user. The device can comprise two temperature instruments on the wearable device and the computer controller or microprocessor of the wearable device includes computer readable instructions for obtaining temperature readings from the instruments or for basing a temperature output to a device indicator by processing the output of the temperature instruments. The device can also incorporate an optical array for monitoring various physiological parameters of the user. The enclosure can be made of a bio-compatible material that is comfortable to wear and extremely light weight while robust enough to endure daily use.

This device can be programmable using a programmer unit as well as over the air using the RF module. The RF antenna can be placed at the rear of the main board to mitigate the risk of interference from other components. The device can communicate with the bridge device using Bluetooth Low Energy (BLE). The device can contain a battery holder underneath the device for a 3.7V coin cell battery which can provide it with a 3-day battery life.

Advantageously, embodiments of the inventive wearable device are adapted and configured for collection of physiological parameters of a user wherein at least one device portion of the wearable device is configured for placement within the axilla of a user. The device portion configured for placement for registering user parameters via the axilla may have an outward size, shape, contour or surface configured for user comfort based on the overall profile, shape, size, flexibility, contour or other feature or characteristic of the wearable device to provide user comfort when positioned against the skin in a portion of the axilla and between the axilla and the arm, including when the in a lowered position against the axilla or when the arm is swinging relative to the axilla such as when walking or running or playing a sport or swimming, or other activities, including during recovery from a surgical procedure.

Figure 19:
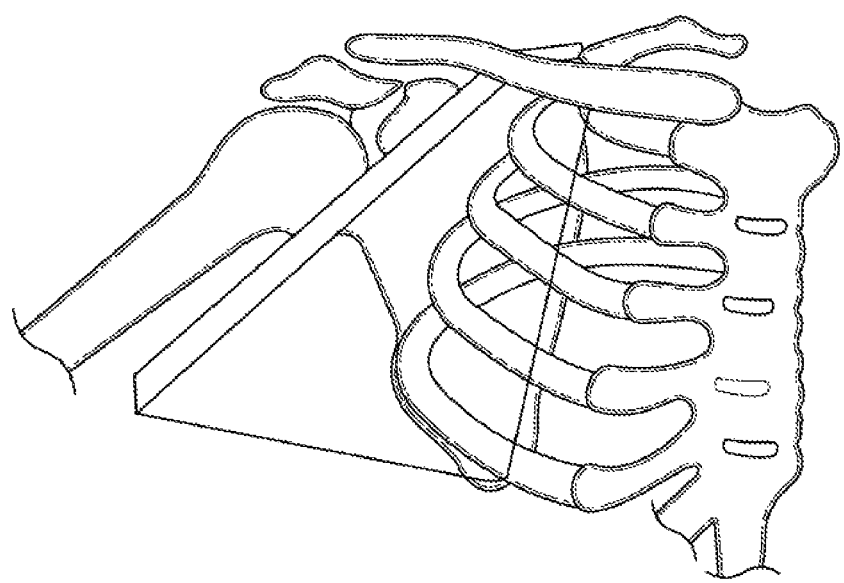
FIGS. 19 and 20 illustrate features of anatomy surrounding the axilla.
Figure 20:
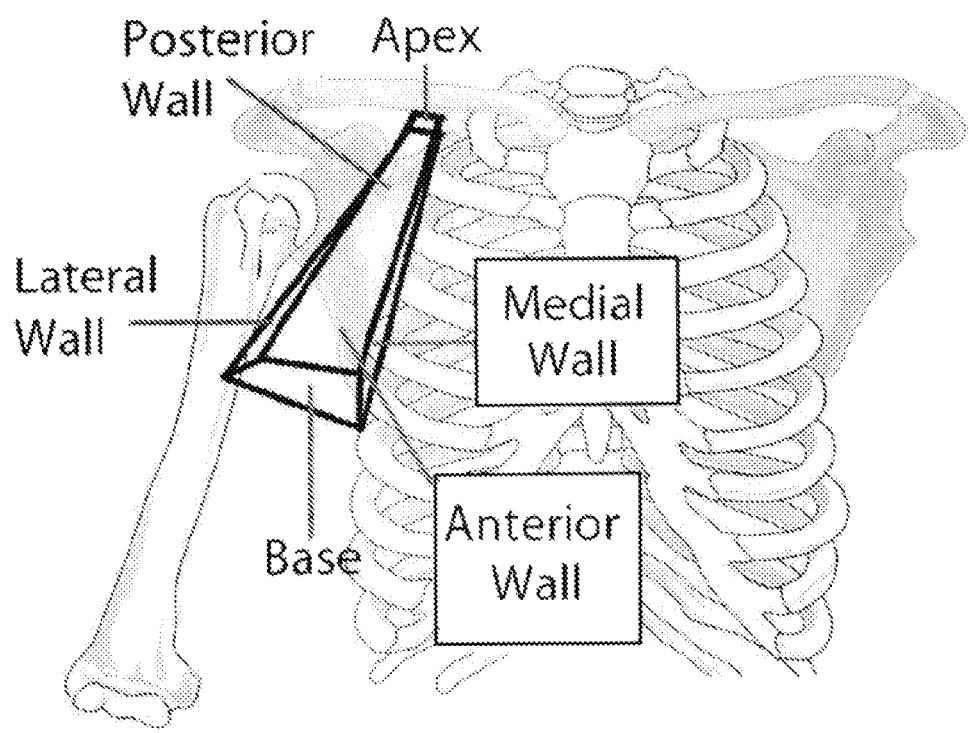

Anatomically, in general, the boundaries of the axilla are appreciated with reference to the perspective provided in the various views in FIGS. 19 and 20. The axilla has an apex, base, and 4 walls (anterior, posterior, medial, and lateral walls). More specifically, the axilla is described,
- superiorly: by the outer border of first rib, superior border of scapula, and posterior border of clavicle;
- medially: serratus anterior and by the ribcage;
- anteriorly: by the pectoralis major, minor and subclavius;
- posteriorly: by the subscapularis above, and teres major and latissimus dorsi below
- laterally: by the intertubercular sulcus (optionally, in some aspects, the coracobrachialis and the short head of the biceps brachii are considered in the axilla.)
- floor/base: by the skin (visible surface of axilla).

As used herein, the wearable device has an enclosure with a first end and a second end, and a central, flexible portion connecting the first end and the second end. The various devices, microelectronics, communication components and power supply are fully contained within the enclosure. Openings in the bottom or user facing surfaces of the enclosure provide access to or physical contact with the skin of the user. In some cases, a skin contacting portion of a device may extend below a bottom most surface of the enclosure. In some embodiments, the bottom most portion is a bottom surface of the enclosure. In other aspects, the bottom portion is the bottom most portion of an adhesive affixed to the lower most portion of the enclosure. In these various embodiments, the skin contacting portion of the device may extend 0.1 mm, 0.2, mm, 0.3 mm, 0.4 mm, 0.5 mm, 0.6 mm below the bottom portion. In the case of obese users, the amount of the device extending below the bottom surface may be adjusted in response to the amount of fat in the axilla of the obese user wherein in use the device is able to detect the physiological parameters of the obese user. In some embodiments, the wearable device top layer of the enclosure is made of foam and the bottom layer is a combination of a plastic film and silicone adhesive. In one aspect, the adhesive is only applied to the bottom surface of the perimeters of the ends of the device. In another aspect, the adhesive is applied along the entire bottom surface of the enclosure in contact with the skin of the user. In other aspects, the adhesive is present on the bottom surface of the end portions of the wearable device, along the perimeter with at least one, more than one, or a series of gaps in the adhesive to increase user comfort. In some aspects, the edge of the enclosure and the adhesive have a sloped shape to reduce the profile of the device or with other shapes to increase user comfort.

In other additional embodiments, the outer surface of the enclosure, an upper or superior aspect of the enclosure, a lower or inferior aspect of the enclosure, a joining or transition section of the flexible portion to an end portion are shaped, sized, configured, contoured, textured, treated, beveled or otherwise modified to increase user comfort or increase the conformability of the wearable device to the anatomical site where the device will be releasable affixed to the user or to increase the conformity of the device to a portion of the skin of the user, a portion of the axilla of the user, a portion of a posterior aspect of the user's chest or a portion of an anterior aspect of the user's chest or other shape to conform with all or a portion of an anatomical site where the wearable device will be placed on the user. In another aspect, the central portion has a nearly constant width from one end to the other end of the wearable device. In another aspect, the central portion has a wider portion nearer one end of the wearable device. In another aspect, the central portion of the wearable device has a decreasing width towards the portion of the device contacting the user axilla.

In some embodiments, the overall length of the device is sufficient to have one end and the associated devices within the axilla and the other end and any associated devices outside of the axilla, or outside of the axilla on an anterior or posterior aspect of the thoracic cavity of the user. In some embodiments, the overall length of the wearable device is more than 115 mm. In some embodiments, the overall length of the wearable device is more than 145 mm. In some embodiments, the overall length of the wearable device is from about 110 mm to about 150 mm. In some embodiments, the overall length of the wearable device is from about 135 mm to about 160 mm. In some embodiments, the area of one end of the device is larger than the area of the other end of the device. In some embodiments, a larger end of the device has an area of 350-700 square mm. In one aspect, the smaller end of the device has an area of 150-250 square mm. In still another aspect, the central portion between the ends is from 70 to 90 mm. In another aspect, the central portion between the two ends is from 90 to 130 mm. In still other aspects, the central portion is sized for an obese user. In other aspects, the length of the central portion is 140 mm, 150 mm or 160 mm.

In some embodiments, the wearable instrument may be provided with additional functionality, features and design characteristics.

In one exemplary configuration, the wearable instrument has electronics completely within the enclosure. Portions of the electronics may be positioned into optimized locations based on use or function with other components of the wearable instrument. For example, a data in port may be placed towards the central portion of the device towards the flexible central portion to shorten the length of a data line from the one or more instruments on the other end of the flexible middle portion. Additionally, or optionally, an output or an indicator of the electronics system may be positioned in proximity to the instrument collecting the data to be displayed again to make the device more compact by shortening data and sensing lines and circuitry or permitting even more compact ASIC instrument designs. In some embodiments, one temperature instrument is adjacent or proximate to an external temperature instrument that provides an output visible when viewing an outer surface of the enclosure. In one aspect, the temperature instrument in positioned on the smallest end portion of the device. In some embodiments, an output based on data collected by one or more temperature instrument of the wearable instrument is visible on a portion of the device designed for placement within an axilla of the user. There can be two temperature instruments on the wearable device, and the computer controller or microprocessor of the wearable device includes computer readable instructions for obtaining a temperature reading from each one of the instruments separately or for basing a temperature output to an instrument indicator by processing the outputs of each of the temperature instruments together. In still other aspects, the wearable instrument contains, within the enclosure, a plurality of instruments that, when the device is positioned with one end in a portion of the axilla of a user, the electronics and the power supply of the wearable device are outside of the axilla. In another aspect, all or a portion of a power supply may be within the portion of enclosure within a portion of the axilla. In still other aspects, the wearable device contains within the enclosure a plurality of instruments that when the device is positioned with one end in a portion of the axilla of a user, the electronics and the power supply of the wearable device are outside of the axilla within the bendable central portion and the other end of the wearable device enclosure. In another aspect, all or a portion of a power supply may be within the bendable central portion of enclosure.

In still other embodiments, the memory of the wearable device includes computer readable instructions for one or more of: collecting, processing or storing within the memory of the wearable device signals from the one or more instruments on the wearable enclosure; methods for compressing the data within the memory; methods for electronic transmission to a computer system electronically linked to wearable device; algorithms specific to the instrument type, data collection type, user physiological parameter being monitored, measured, collected or processed by the wearable device; and any specific factors, variables, calibration information, software, firmware or middle ware for recommended or specifically configured use of a temperature instrument, an ECG instrument, a next-generation optical instrument including infrared, red and green portions of the spectrum, a PPG instrument, an instrument having an LED based instrument, a micro machined (MEMS) or nanotechnology instrument (Nano instrument) or other component within the enclosure that when worn by a user detects one or more physiological parameters of the user. In specific embodiments, the enclosure contains an appropriate situated PPG instrument and the memory of the device controller or microcontroller contains computer readable instructions for conducting Photo Plethysmography processing of outputs from the PPG instrument to monitor pulse, R-R interval, respiration rate, cardiac output, blood pressure and blood oxygen, alone or in combination or consideration of contemporaneously collected, sequentially collected or simultaneously collected instrument data from another instrument on the wearable device.

Additionally or optionally, the wearable device also includes one or more of a suitable communications component to transfer data collected by the instruments, processing results from the electronics, data stored within the memory of the device or any other electronic signal collected or produced by the device to an external site including another computer whether connected by local network as in a hospital setting or via suitable connection to a cloud based or remote networked location or to a tablet, smart phone, or other mobile device adapted or configured via app or other software for communication with the wearable device.

Unless defined otherwise, all technical and scientific terms used herein have the same meaning as commonly understood to one of ordinary skill in the art to which the presently disclosed subject matter belongs. Although any methods, instruments, and materials similar or equivalent to those described herein can be used in the practice or testing of the presently disclosed subject matter, representative methods, instruments, and materials are now described.

The Bridge Device

The bridge device can serve as a connection between the device and the Cloud Database. The bridge device is AC-Powered and has a battery as backup. It communicates with the device via an RF protocol and is connected to the cloud database via WiFi/Ethernet/Mobile (3G/LTE) etc. It also contains a memory module that can store data when a connection with the Cloud Database is lost. The bridge device contains Firmware that manages processes like device pairing and "hand-shake" to ensure that when a user moves out of range of one bridge device, the device is paired with the next bridge device in range. Through this "hand-shake" process, the bridge device ensures no loss of data packets to the cloud database.

The data is sent via the bridge device to a cloud database and is stored for further analysis. 256 bit Encryption is used to protect the data sent between the wearable instrument, the bridge device, the cloud database and the device used to display the data. The cloud database is HIPAA compliant and Sock 2 Type 2 certified and manages the upload, processing and storage of device data. As shown in FIG. 5, data can be sent to a screen at the nurse's station, a hospital's electronic medical record, and any connected smart-device without the need for those devices to be in close proximity to the wearable instrument. FIG. 5 depicts a screen displaying data received from multiple bridge devices and sensor devices. The data received includes patient pulse 502, saturation 504, respiration 506, and temperature. API accessibility has been built into the cloud database to allow 3rd parties to securely access the data. Authorized clinicians and medically qualified personnel can configure the system parameters via the API to generate notifications of changes in measured data. With the connection to the secure server, a notification is triggered when configured vital sign data parameters are exceeded. Notifications are transmitted to a generic display device (i.e. smartphone, tablet, PC, monitor or 3rd party application). The data on the Cloud Database can be curated and packaged to be provided to any 3rd party like hospitals, pharmaceutical companies etc. Data analysis algorithms run on the cloud database to analyze collected data and derive further insights.

The Vitls App

The Vitls App can make user data available in an intuitive app.

Figure 6:
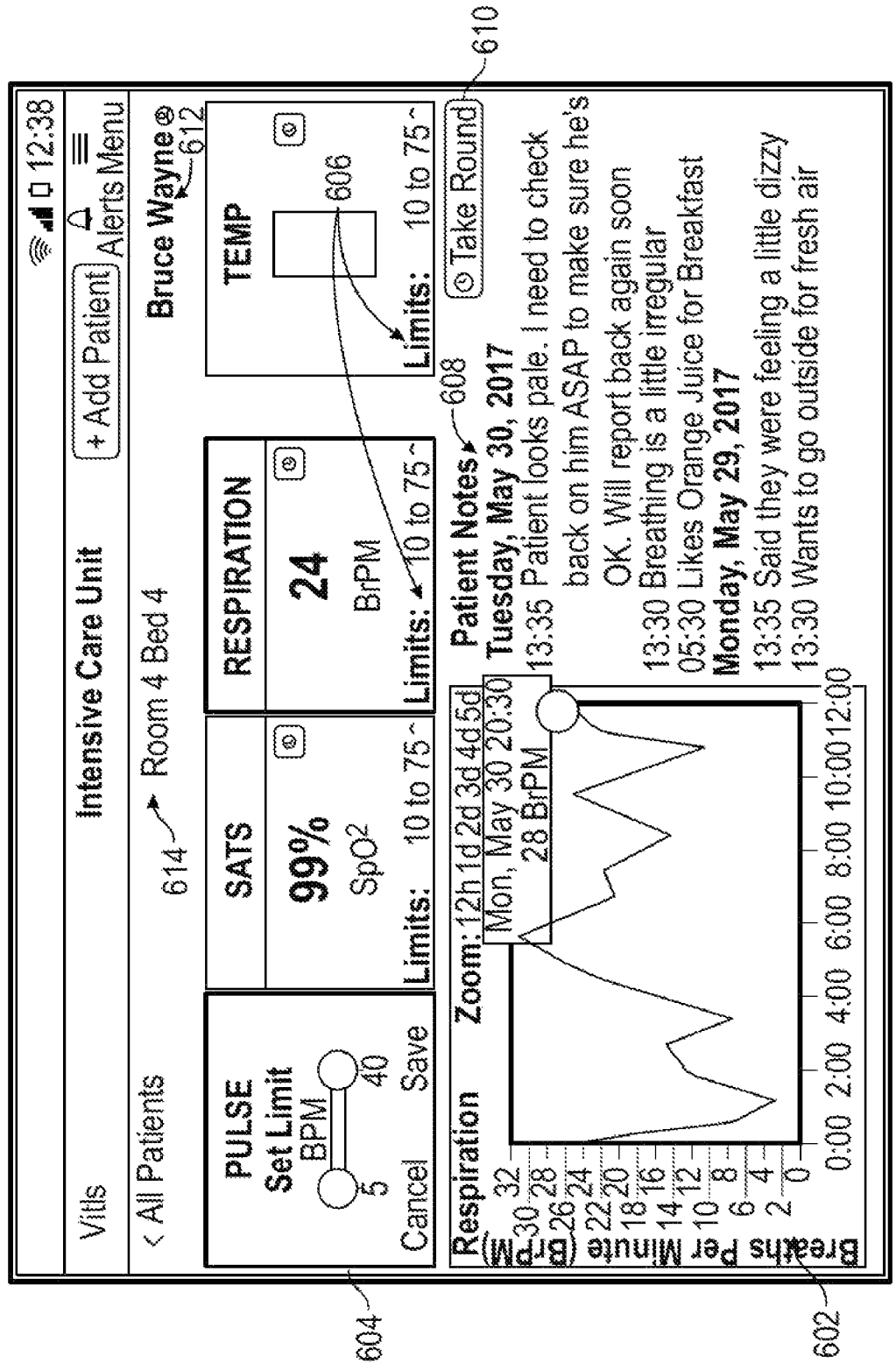

The Vitls App can display vital sign data on any connected device. The main dashboard displays all the devices that are currently in use in the facility, per ward (FIG. 5). From the main dashboard, a user can select an individual device/user to view more detailed data regarding that user. In FIG. 6, one user has been selected. The user specific screen shows the parameters from the dashboard, and also is able to show historic data for a parameter, such as is shown in the respiration graph. The user can also set acceptable limits for a particular parameter, as shown in the Pulse 'set limits' screen 604. To access this screen, a user can select the 'Limits' section 606 below the desired parameter. If the parameter moves outside of the set limits, an alarm will be triggered to notify the user of the change. Additionally, a 'patient notes' section 608 allows a user to quickly and easily see patient specific notes. This feature can be especially helpful across shifts to get an easily accessible update on the patient. A 'take round' section 610 allows for additional notes to be added when a nurse is doing patient observation during rounds. At the top of the screen, the patient name 612 and location 614 are also shown.

The layout and colors used enables users to, at a glance, assess the status of a user wearing the instrument. The colors and layout of the app can be customized for each individual hospital to comply with their workflow. In some embodiments, patients are divided into different groups. Different indicators, such as color, can be used to differentiate between the groups. For example, patients can be divided into the following sections with different color indicators—Unstable (Red—when one or more vital signs have exceeded the limits/ranges previously set), At-Risk (Orange—when one or more vital signs are within a certain percentage of the set limits/ranges) and Stable (Green—when all vital signs are within the preset minimum and maximum limits/ranges). In FIGS. 6 and 7, the various parameters are color coded according to the preceding description.

Referring to FIG. 7, at the top of the screen is a location indicator 702, displaying which unit the dashboard is monitoring. In FIG. 7, it is the pediatric ward. An 'add patient' button 704 allows a user to add an additional monitored patient. An 'alerts' section 706 allows a user to see all the alerts. Finally, a menu button 708 is also displayed.

Figure 9:
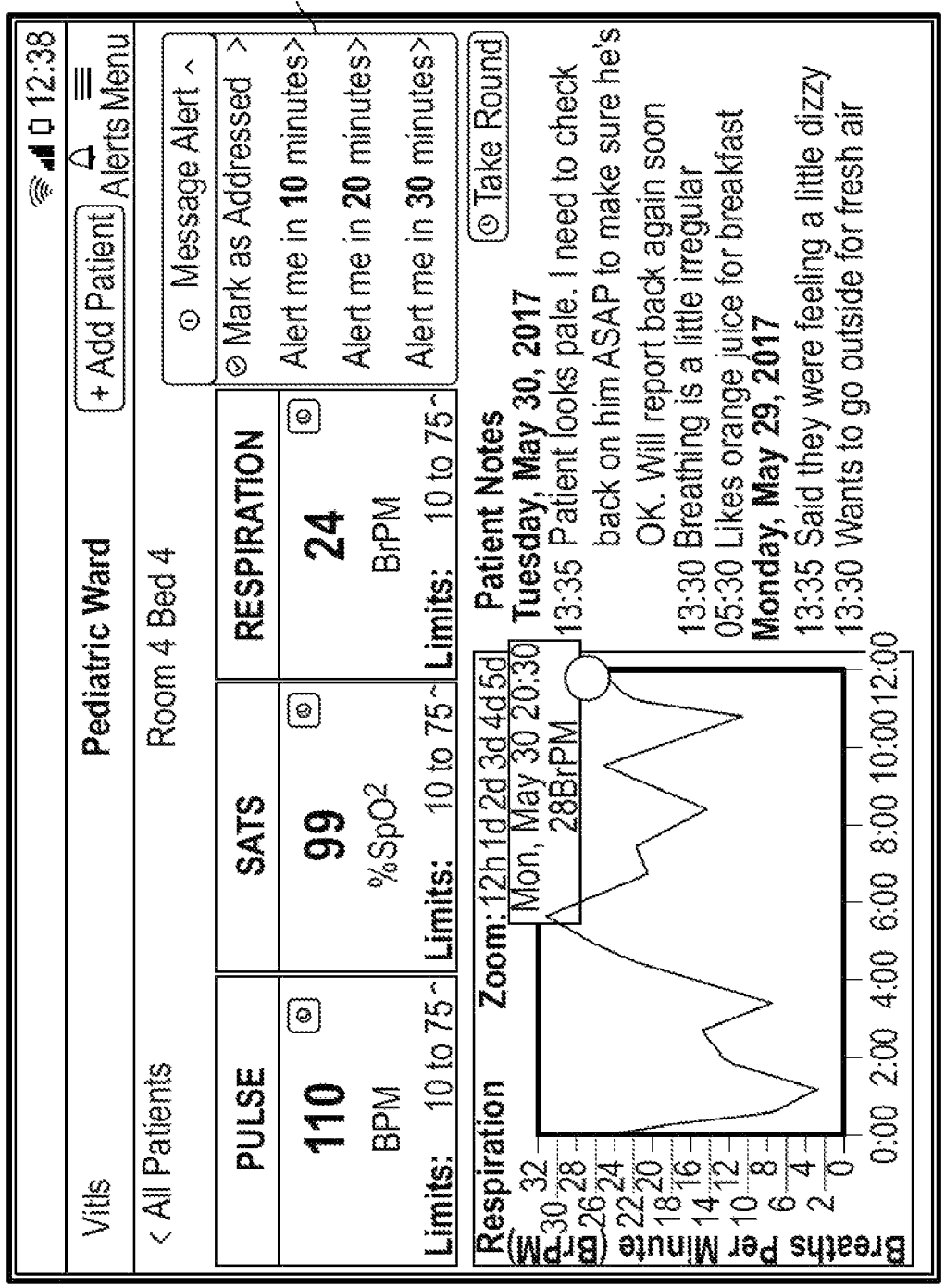
Figure 10:
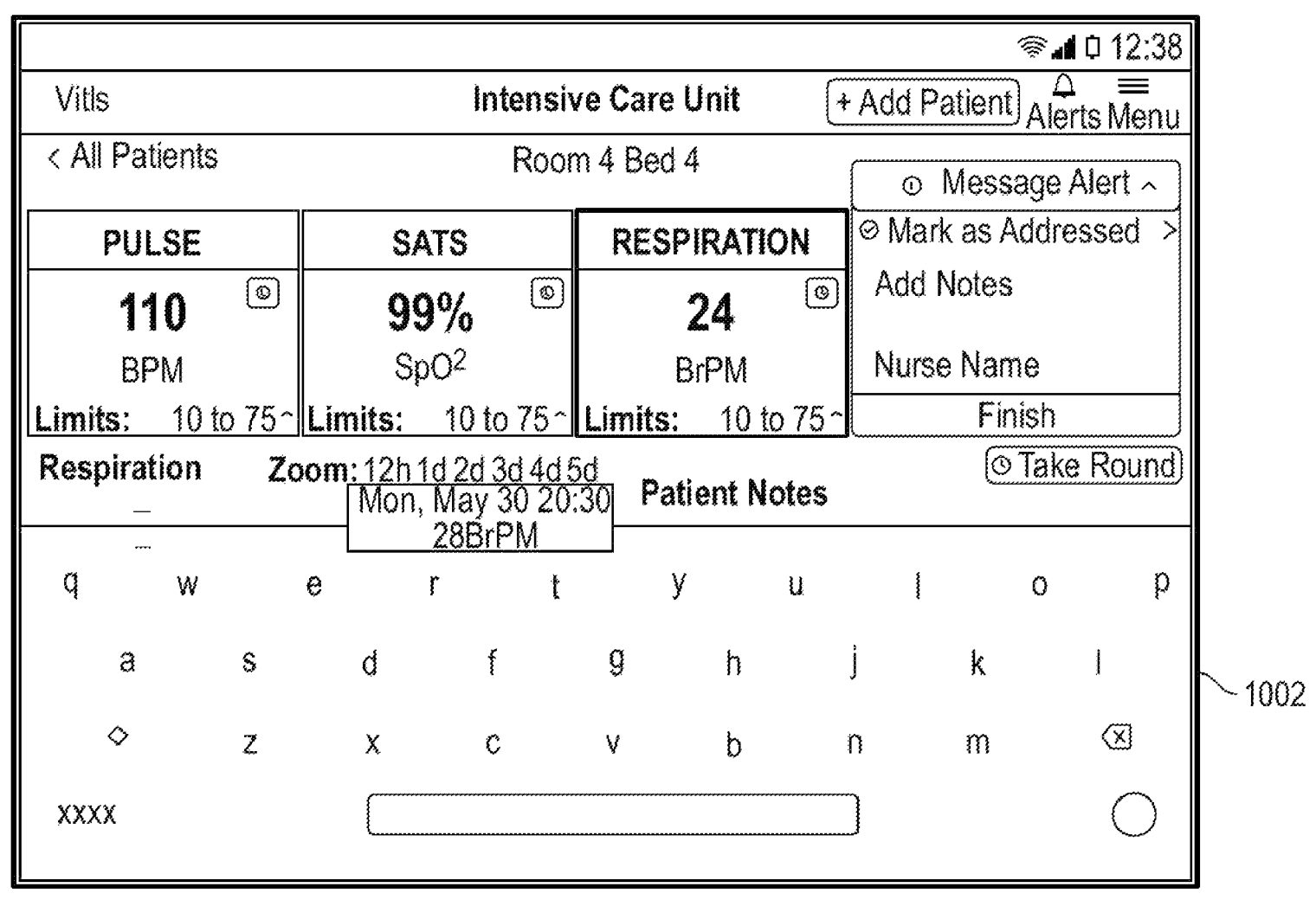

Alerts 802 are displayed in either orange or red tabs at the top of the main dashboard, as shown in FIG. 8. When an alert is triggered, the healthcare provider mutes the alert, indicating that the user is being tended to, and proceeds to tend to the user (FIG. 8). When finished with the user, they add a note to the user page outlining what happened, what treatment was administered as well as their identification number (FIG. 9). All this data is recorded in the cloud for analysis. FIG. 9 also shows a 'manage alert' section 902 that allows the alert to be marked as addressed (shown in FIG. 10) or set the system to repeat the alert at a given time. FIG. 10 shows a screen with a keyboard 1002 allowing for text entry of a note describing how the alert was addressed.

Figure 11:
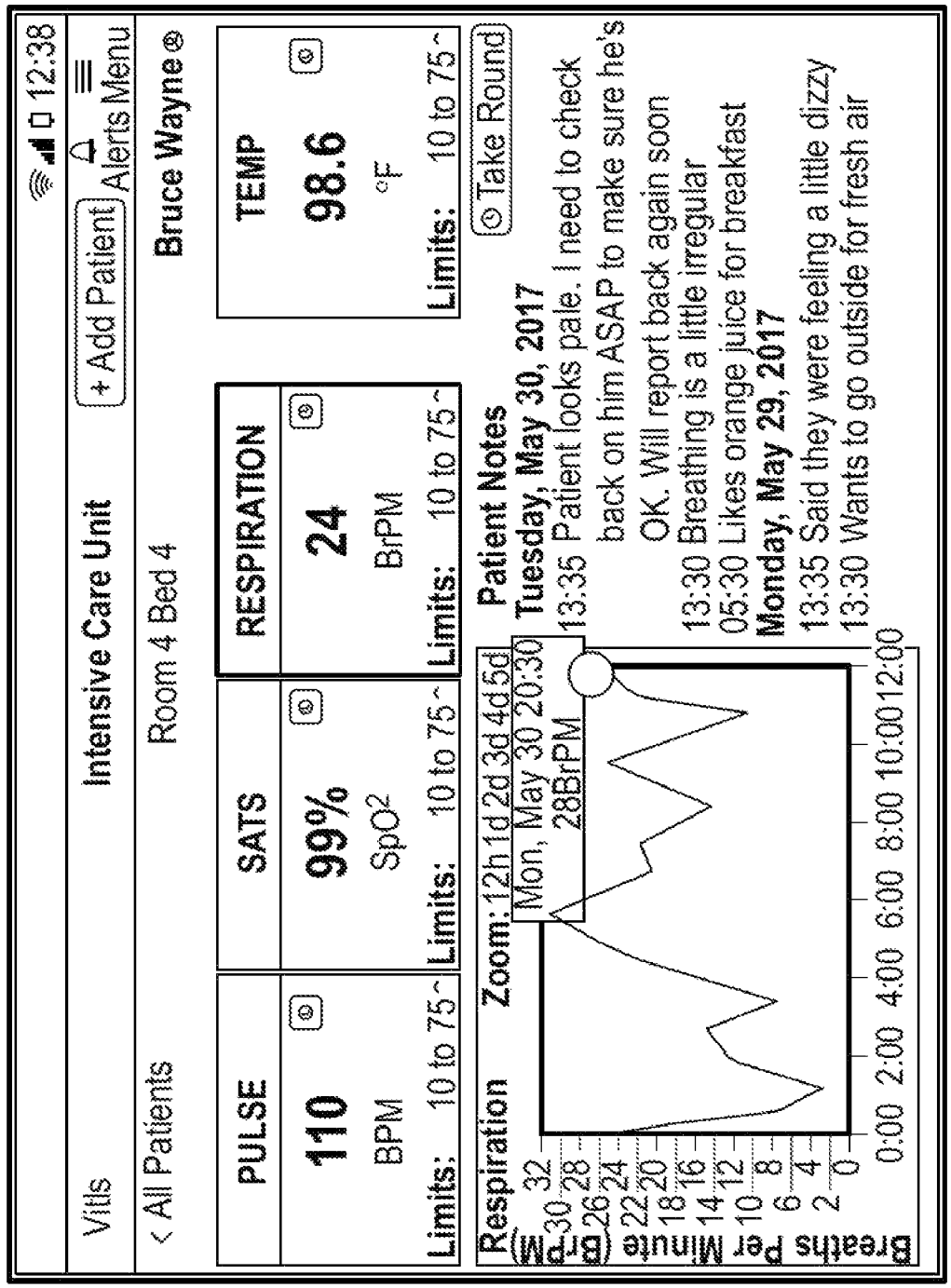

FIG. 11 shows the patient screen after the alert had been marked as addressed The Patient Screen displays real-time vital signs data as it is being collected by the device. Vital signs are also displayed in Red, Orange and Green depending on the status. Active Alerts are visible on this page for the user page being viewed as well as any other users who might trigger an alert. As described above, data can also be viewed in a graph that displays historic data over 12 hours, 1 day, 2 days, 3 days, 4 days or 5 days for any selected vital sign.

Added functionality includes the option to print out the user data, view historic alerts and change the current alert settings.

It will be appreciated that an app configured to be used with the devices disclosed herein can comprise any combination of the features described above with respect to the app.

Figure 17:
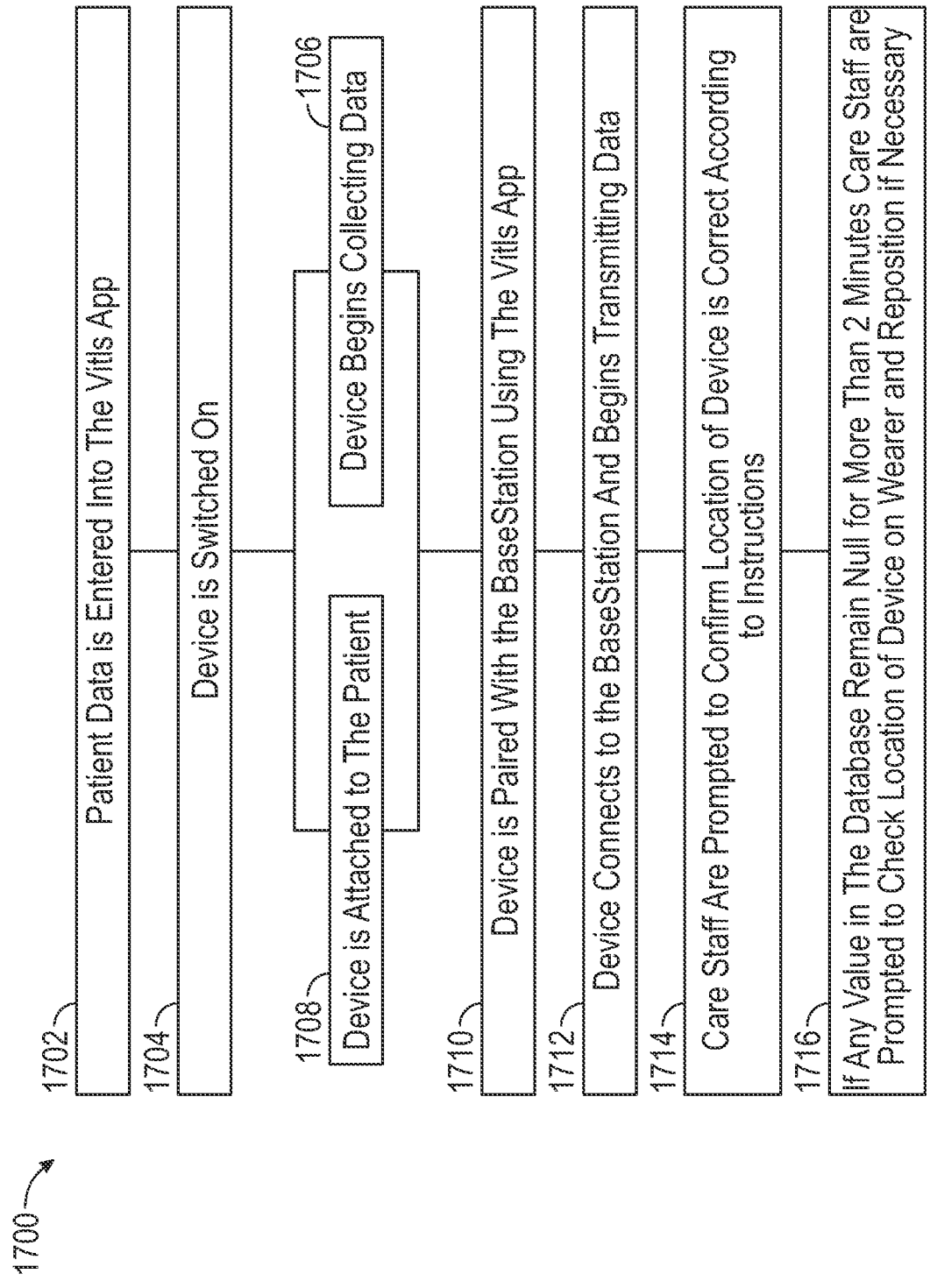
FIG. 17 depicts an embodiment of a method of using a wearable device.

FIG. 17 shows an embodiment of a method 1700 for using the devices disclosed herein. The method comprises entering data into the App, as shown at box 1702. The device can be switched on, as shown at box 1704. The device can be attached to the patient, as shown at box 1708 and switched on, as shown at box 1706. The device is paired with the base station using the app, as shown at box 1710. The device connects to the base station and begins transmitting data, as shown at box 1712. Care staff are prompted to confirm that the location of the device is correct, according to instructions on the screen, as shown at box 1714. If any value in the database remains null for more than a set amount of time (e.g., 2 minutes), the care staff is prompted to check the location of the device on the wearer and reposition if necessary.

FIG. 18 shows an embodiment of a diagnostic check 1800 on device components. The device can check the first temperature sensor, as shown at box 1802. The device determines whether the sensor is functioning correctly, as shown at box 1804. If it is not, an alert is sent to the base station, as shown at box 1824. If it is, the device checks the second temperature sensor, as shown at box 1806. The device determines whether the sensor is functioning correctly, as shown at box 1808. If it is not, an alert is sent to the base station, as shown at box 1826. If it is functioning correctly, the device checks the optical sensor array, as shown at box 1810. The device determines whether the sensor is functioning correctly, as shown at box 1812. If it is not, an alert is sent to the base station, as shown at box 1828. If it is functioning correctly, the device checks the accelerometer, as shown at box 1814. The device determines whether it is functioning correctly, as shown at box 1816. If it is functioning correctly, an alert is sent to the base station, as shown at box 1830. If it is functioning correctly, the device checks the flash memory as shown at box 1818. If it is not functioning correctly, the device sends an alert to the base station, as shown at box 1832. If it is, the diagnostic check ends, as shown at box 1822.

Example Applications for the Monitoring Device

The device can be used to monitor patients in the Hospital Emergency Department who are waiting for treatment and are currently only being spot-checked whenever a nurse or technician is available which would sometimes be every 2 hours. Many of these patients crash in the waiting room, especially pediatric patients because waiting times in the ED at peak times can be up to 6 hours. This results in resources allocated to the patient who crashed which just increases waiting time. With the device disclosed herein, patients waiting in ED can be continuously monitored and "constantly" be in triage. The sensor device can be used to determine the "baseline" of the patient and as soon as nurses at the nursing station notice a patient is deteriorating, they can call that patient to the front to be treated. This way of triage can shorten waiting periods, reduce the number of patients crashing in ED and increase throughput for the ED which means more profit for hospitals. In this embodiment, the device can be configured to monitor at least body temperature, pulse, blood oxygen (SpO$_2$), and respiration. The device can improve workflow by eliminating the need for technicians or nurses to monitor patients. Nurses can focus on getting patients treated and out the door. This can significantly impact waiting times. No patients crashing in the ED and shorter waiting periods means a better satisfaction score for the hospital and better rating which results in more business.

The device can also be used to monitor patients of general floors. Seventy five percent of adverse events and preventable deaths in hospitals occur outside the ICU in beds that are intermittently monitored. On the General Floor, patients are currently being monitored every 4 hours. Nurses have an average of 8 patients to take care of during a shift and every 4 hours, it takes a nurse up to 15 minutes to check each patient, write the vital signs down and sterilize the equipment before moving on to the next patient. Worse, nurses often do not have time to sterilize the equipment which could result in cross contamination between patients. This is a huge financial risk for hospitals in loss of business due to the entire floor needing sterilization as well as risk of liability. After checking on the 8 patients, the nurse does data input, manually entering the data into the electronic medical record. A recent study proved that 60% of data that is manually entered into the medical record contains errors. Human error is a big risk and can lead to misdiagnosis etc. With the wearable devices disclosed herein, patients can be continuously monitored and, after determining a patient's baseline, deterioration can be picked up as soon as it happens. This results in early detection which leads to reduction in treatment costs, length of stay and readmission. The nurse also doesn't have to spend any time monitoring the patient and can focus on patient satisfaction and all the other work as nurses are notoriously inundated with work. If a patient doesn't have to be woken up for vital sign checks, they will sleep better, heal faster and be much happier. In this embodiment, the device can be configured to monitor at least body temperature, pulse, blood oxygen (SpO$_2$), respiration, and blood pressure. Monitoring using the device can improve workflow by eliminating the need for nurses to spend any time monitoring the patient and doing data input into the EMR. This allows nurses to focus on patient satisfaction and all the other work, as nurses are notoriously inundated with work. If a patient doesn't have to be woken up for vital sign checks, they will sleep better, heal faster and be much happier. This means a better satisfaction score for the hospital and better rating which results in more business.

In some embodiments, the device is used for monitoring postoperative patients that are at risk of developing respiratory complications (e.g., within one week after surgery). Acute respiratory failure is a relatively common complication in surgical patients, especially after abdominal surgery. Non-invasive ventilation (NIV) is increasingly used in the treatment of acute respiratory failure. With the devices disclosed therein these patients can be monitored continuously after surgery using an unobtrusive device that the patient can continue wearing post-discharge. In this embodiment, the device can be configured to monitor at least Body temperature, pulse, blood oxygen (SpO$_2$), respiration, heart rate variability. This device can improve workflow by allowing fewer machines for postoperative patients. No nurse or technician is needed to disconnect the patient from the machine and to move the machine back to the OR.

In some embodiments, the device is used for monitoring postsurgery patients at risk for sepsis. Surgery is a procedure that affects your body in many ways aside from the actual reason for the operation. Any type of surgery from an appendectomy (Sepsis and Appendicitis) to a face lift to a Cesarean section (Sepsis and Pregnancy) exposes your body to infection and a fair number of complications, some of which could develop into sepsis.

Sometimes incorrectly called blood poisoning, sepsis is the body's often deadly response to infection. Sepsis kills and disables millions and requires early suspicion and rapid treatment for survival. Sepsis and septic shock can result from an infection anywhere in the body, such as pneumonia, influenza, or urinary tract infections. Worldwide, one-third of people who develop sepsis die. Many who do survive are left with life-long complications, such as post-traumatic stress disorder (PTSD), chronic pain and fatigue, organ dysfunction and/or amputations. Each case costs hospitals an average of $20,000 and hospitals are also penalized for each case. Patients often have lifelong complications because of sepsis. With the wearable device disclosed herein, patients can be monitored continuously post-surgery and nurses and physicians can be notified of any indicators of possible sepsis infection. Patients can also take the device home to be monitored until they are past the risk period. In this embodiment, the device can be configured to monitor at least body temperature, pulse, blood oxygen ($SpO_2$), heart rate variability, respiration.

In some embodiments, the device can be used to monitor chronically ill patients. Chronically ill patients already have a reduced quality of life, even more so because they spend a lot of time on monitors. Because of the monitors, they do not have freedom of movement and if they have to do rehab, they can only do so for short periods of time. With the wearable monitors disclosed herein, patients can lead semi-normal lives and fully participate in rehab. In this embodiment, the device can monitor at least body temperature, pulse, blood oxygen ($SpO_2$), respiration, heart rate variability.

In some embodiments, the device can be used to monitor blood volume in women giving birth and general surgery patients. Circulating blood volume (CBV) is an important, but often unmeasured, variable in patients undergoing major surgery and in intensive care. Severe volume depletion leads to clearly recognizable clinical shock that requires urgent intervention. With the devices disclosed herein, one can the change in blood volume using the optical sensor. When the change becomes significant, physicians can be notified and they can provide the patient with extra blood. In this embodiment, the device can be configured to monitor at least pulse, blood oxygen ($SpO_2$), respiration and blood volume. A visual inspection is currently being done to assess blood loss of a patient in surgery. The device can provide a more certain way of measuring this and reduce risk significantly.

In some embodiments, the device can be used to monitor cardiac output through pulse contour analysis. Cardiac output is the product of the heart rate (KR), or the number of heart beats per minute (bpm), and the stroke volume (SV), which is the volume of blood pumped from the ventricle per beat; thus, CO=HR×SV. It can be measured in different ways, for example using a flow meter. The clinician inserts this device into the artery that sends blood to the lungs to pick up oxygen. This is a very invasive, costly and risky procedure. With the device disclosed herein, the sample rate of the optical sensor can be increased to monitor blood flow and identify a dicrotic notch, a small, downward deflection observed on the down stroke of an arterial pressure waveform. It represents closure of the aortic or pulmonic valve at the onset of ventricular diastole. The changes in blood volume are measured in the peripheral circulation beneath the skin by means of Photoplethysmography (PPG). Light from the PPG sensor reflects differently in oxyhemoglobin compared to deoxyhemoglobin and the sensor can detect these changes in light absorption. The changes in the blood volume caused by the pressure pulse can be detected by the PPG sensor using infrared light. It is known that absorption of deoxyhemoglobin and oxyhemoglobin is maximum for 660 nm and 860 nm respectively. Oxyhemoglobin and deoxyhemoglobin concentration change can be detected by measuring the mean square spectrum for 660 nm and 860 nm respectively. In this embodiment, the device can be configured to monitor at least pulse, blood oxygen ($SpO_2$), respiration, cardiac output measurement. This is a novel, non-invasive way to monitor cardiac output on the chest. It would be extremely advantageous to be capable of monitoring cardiac output accurately, continuously and reliably, in such a non-invasive way.

In some embodiments, the device can be used to monitor telehealth patients. By wearing the device 24 hours before a telehealth visit, physicians will receive relevant, real-time data on the patient they are consulting with. This will enable them to make more accurate diagnoses and reduce their liability risk. In this embodiment, the device can be configured to monitor at least Body temperature, pulse, blood oxygen ($SpO_2$), respiration, and heart rate variability.

In some embodiments, the device can be used to monitor pilots. The navy and army has had a problem with pilots developing hypoxia during flight in certain fighter and training jets. Hypoxia is a deficiency in the amount of oxygen reaching the tissues in the body. Pilots who realize too late that they are hypoxic, feint and sometimes crash their planes. By using the device disclosed herein, the pilot or those monitoring the pilot can be alerted of a drop in oxygen and can push more oxygen through their On-Board Oxygen Generation System (OBOGS). In this embodiment, the device can be configured to monitor at least Body temperature, pulse, blood oxygen ($SpO_2$), respiration, and heart rate variability.

In some embodiments, the device can be used to monitor wounded soldiers. Medics are often far away when soldiers are on a mission. With the device, a medic can receive real-time vitals of a wounded soldier while the soldier is waiting for a medevac. Knowing what to expect could save minutes and possibly lives. In this embodiment, the device can be configured to monitor at least Body temperature, pulse, blood oxygen ($SpO_2$), respiration, heart rate variability, and blood pressure.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "user-specific," "customized," and/or "adaptive," when used in reference to a glenoid implant or humeral implant, can be used interchangeably and can in some embodiments refer to the specialization of such features taking into consideration factors specific to a user to be treated, including for example characteristics acquired from pre-operative analysis and planning or a selected reverse or anatomic shoulder procedure.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of monitoring a user, comprising
removably attaching a first end and a second end of a device to the skin of a user, wherein the first end and the second end connect by an intermediate flexible portion, wherein the first end is a main board and the second end is a sensor board and a bottom surface of the first end, the second end, and the intermediate flexible portion comprises an adhesive,
wherein removably attaching the device to the skin of the user comprises extending the first end into a chest of the user and using an indicator on the second end to position a portion of the second end on an axilla of the user,
wherein the intermediate flexible portion curves around a curve of the chest and transfers data between the sensor board and the main board;
monitoring one or more physiological parameters of the user, including at least one of body temperature, heart rate, heart rate variability, RR interval, respiration rate, blood oxygen levels (SpO2), blood pressure, cardiac output, body fluid analysis, sleep cycles, movement and proximity of the device to the skin of the user; and
executing machine executable instructions configured to cause the device to send user data to a remote database.

2. The method of claim 1, wherein the indicator is a midaxillary line indicator that is used to position the second end on the midaxillary line of the user.

3. The method of claim 1, wherein removably attaching the device to the skin of the user comprises using the first end that is larger than the second end.

4. The method of claim 1, wherein removably attaching the device to the skin of the user comprises locating the first end vertically in line, above, or past the nipple.

5. The method of claim 1, wherein the main board comprises a plurality of instruments including a communications module.

6. The method of claim 5, wherein the sensor board comprises a plurality of instruments including an optical array.

7. The method of claim 6, further comprising using the intermediate flexible portion to transmit user data collected from the optical array of the sensor board to the communications module of the main board.

8. The method of claim 1, wherein removably attaching the device to the skin of the user comprises conforming the device that is a flexible circuit board to the skin of the user.

9. The method of claim 1, wherein monitoring one or more physiological parameters of the user comprises using a battery located in the device that powers the device for more than 70 hours of continuous monitoring of the one or more physiological parameters of the user.

10. The method of claim 1, wherein monitoring one or more physiological parameters of the user comprises using a battery located in the device that powers the device for more than 140 hours of continuous monitoring of the one or more physiological parameters of the user.

11. The method of claim 1, wherein monitoring one or more physiological parameters of the user comprises continuous monitoring of one or more physiological parameters of the user.

12. The method of claim 11, wherein the user is a postoperative patient.

13. The method of claim 11, wherein the user is a chronically ill patient.

14. The method of claim 11, wherein the user is a telehealth patient.

15. The method of claim 11, wherein the user is a pilot or a soldier.

16. The method of claim 1, further comprising entering user data into an app configured for electronic interaction with the device.

17. The method of claim 16, further comprising pairing the device with a base station using the app.

18. The method of claim 17, further comprising executing machine executable instructions configured to cause the device to transmit data to the base station.

19. The method of claim 17, further comprising executing machine executable instructions configured to cause the app to prompt a clinician to confirm placement location of the device.

20. The method of claim 1, wherein the intermediate flexible portion further comprises a flexible battery.

* * * * *